United States Patent
Bold et al.

(10) Patent No.: US 7,294,633 B2
(45) Date of Patent: Nov. 13, 2007

(54) OXAZOLO-AND FUROPYRIMIDINES AND THEIR USE IN MEDICAMENTS AGAINST TUMORS

(75) Inventors: Guido Bold, Gipf-Oberfrick (CH); Paul W Manley, Arlesheim (CH); Andreas Martin-Kohler, Basel (CH); Urs Séquin, Therwil (CH)

(73) Assignee: Novartis AG, Basel (CH)

( * ) Notice: Subject to any disclaimer, the term of this patent is extended or adjusted under 35 U.S.C. 154(b) by 115 days.

(21) Appl. No.: 10/476,818

(22) PCT Filed: May 13, 2002

(86) PCT No.: PCT/EP02/05241

§ 371 (c)(1),
(2), (4) Date: Nov. 4, 2003

(87) PCT Pub. No.: WO02/092603

PCT Pub. Date: Nov. 21, 2002

(65) Prior Publication Data

US 2004/0152892 A1   Aug. 5, 2004

(30) Foreign Application Priority Data

May 14, 2001 (CH) .................................. 0873/01

(51) Int. Cl.
| | |
|---|---|
| *C07D 487/04* | (2006.01) |
| *C07D 491/048* | (2006.01) |
| *C07D 413/06* | (2006.01) |
| *A61N 43/54* | (2006.01) |
| *A61N 31/519* | (2006.01) |
| *A61N 31/5355* | (2006.01) |
| *A61N 31/496* | (2006.01) |
| *A61P 35/04* | (2006.01) |

(52) U.S. Cl. ................. 514/260.1; 514/234.5; 514/252.16; 544/255; 544/278; 544/117

(58) Field of Classification Search ............... 544/255, 544/278; 514/260.1
See application file for complete search history.

(56) References Cited

U.S. PATENT DOCUMENTS

| 5,227,387 A | 7/1993 | Dreikorn et al. |
| 6,096,749 A | 8/2000 | Traxler et al. |

FOREIGN PATENT DOCUMENTS

| EP | 0 459 611 A | 12/1991 |
| WO | WO 200232872 A1 * | 4/2002 |

OTHER PUBLICATIONS

Patil, Vemanna D.; Townsend, Leroy B., Journal of Heterocyclic Chemistry, 8(3), 503-5 (English) 1971.*

* cited by examiner

*Primary Examiner*—Brenda L. Coleman
*Assistant Examiner*—Susanna Moore
(74) *Attorney, Agent, or Firm*—Novartis AG; Mark Baron

(57) ABSTRACT

The invention relates to pharmaceutically acceptable compounds of formula I, wherein the radicals have the significances given in the description. Compounds of formula I are useful against tumor diseases

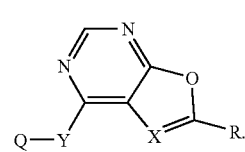

(I)

12 Claims, No Drawings

OXAZOLO-AND FUROPYRIMIDINES AND THEIR USE IN MEDICAMENTS AGAINST TUMORS

SUMMARY OF THE INVENTION

The invention relates to oxazolo- and/or furopyrimidine derivatives, intermediates and processes for their production, pharmaceutical formulations comprising these compounds, and their usage as medicaments or in the preparation of medicaments.

BACKGROUND TO THE INVENTION

Tumour diseases are one of the most important causes of death in industrialised countries. Very great efforts have been made to provide effective compositions and methods of treating tumours. Owing, in particular, to the large number and wide variation of possible tumour diseases, there is a constant need for new pharmacologically active compounds and compositions, which, because of their active substances, are either suitable for treating as many tumour diseases as possible or alternatively are suitable for treating specific tumour diseases. In addition, there are a number of further proliferative diseases or diseases based on missing or defective physiological regulation.

DETAILED DESCRIPTION OF THE INVENTION

The invention relates to a compound of formula I,

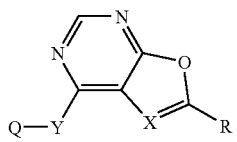

(I)

wherein X either signifies nitrogen, or a carbon atom bearing a radical A;

A signifies hydrogen or —COOW, wherein W is hydrogen or alky, aryl, heterocyclyl or cycloalkyl, whereby each of these radicals is unsubstituted or substituted;

Y is NR', S or O, whereby R' signifies hydrogen or alkyl;

R signifies alkyl, aryl, heterocyclyl, cycloalkyl, aryl-alkyl, heterocyclyl-alkyl or cycloalkyl-alkyl, whereby each of these radicals is unsubstituted or substituted; or it is COOR', COR' or CONR'R", wherein R' and R", independently of one another, are hydrogen or alkyl, aryl, heterocyclyl, cycloalkyl, aryl-alkyl, heterocyclyl-alkyl or cycloalkyl-alkyl, whereby each of these radicals is unsubstituted or substituted; and Q is aryl, aryl-alkyl, heterocyclyl, heterocyclyl-alkyl, cycloalkyl or cycloalkyl-alkyl, which are respectively unsubstituted or substituted;

or a salt thereof, as well as intermediates and processes for the production thereof, pharmaceutical formulations comprising these compounds, as well as their usage as medicaments or in the preparation of medicaments (pharmaceutical preparations).

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either unbranched or branched with single or multiple branching.

Where the plural form is used for compounds, salts, and the like, this is taken to mean also a single compound, salt, or the like ("alone" as an indefinite article or as a numeral).

Asymmetric carbon atoms that are optionally present in the substituents may exist in the (R), (S) or (R,S) configuration, preferably in the (R) or (S) configuration. The present compounds may thus exist as mixtures of isomers or as pure isomers, preferably as pure diastereoisomers or enantiomers.

Alkyl is preferably an alkyl radical with 1 to 20, especially 1 to 10, carbon atoms, preferably lower alkyl, especially methyl. Alkyl is unbranched or has single or multiple branching. Alkyl is unsubstituted or is substituted by one or more, preferably up to three, especially 1 or 2, substituents, selected, independently of one another, from those named below as substituents for aryl.

Lower alkyl is unbranched or has single or multiple branching, and is in particular methyl or ethyl, or also n-propyl, isopropyl, n-butyl, sec.-butyl or tert.-butyl.

Aryl is preferably an aromatic radical with 6 to 18, preferably 6 to 14 carbon atoms, especially phenyl, naphthyl, fluorenyl or phenanthrenyl, whereby aryl, especially the said radicals, may be unsubstituted or substituted by one or more substituents, preferably up to three, primarily one or two substituents, selected from amino; lower alkylamino; N,N-di-lower-alkylamino; amino lower alkyl; lower alkylamino lower alkyl; N,N-di-lower alkyl-amino lower alkyl; lower alkanoylamino, especially acetylamino; halogen, especially fluorine, chlorine or bromine; lower alkyl, especially methyl or also ethyl or propyl; lower alkenyl; phenyl; naphthyl; halogen lower alkyl, especially trifluoromethyl; hydroxy; lower alkoxy, especially methoxy or also ethoxy; lower alkenyloxy; phenyl lower alkoxy, especially benzyloxy; lower alkanoyloxy; carbamoyl lower alkoxy; carboxy lower alkoxy; phenyl lower alkoxycarbonyl lower alkoxy; mercapto; nitro; carboxy; lower alkoxycarbonyl; phenyl lower alkoxycarbonyl; cyano; $C_8$-$C_{12}$-alkoxy, especially n-decyloxy; carbamoyl; lower alkyl-carbamoyl, such as N-methyl- or N-tert.-butylcarbamoyl; N,N-di-lower alkylcarbamoyl; N-mono-or N,N-diphenyl lower alkylcarbamoyl; lower alkanoyl, such as acetyl; phenyloxy; halogen lower alkyloxy, such as trifluoromethoxy or 1,1,2,2-tetrafluoroethyloxy; lower alkoxycarbonyl, such as ethoxycarbonyl; lower alkylpiperazinylcarbonyl; morpholinylcarbonyl; lower alkylpiperazinyl lower alkyl; morpholinyl lower alkyl; lower alkylmercapto, such as methylmercapto; halogen lower alkylmercapto, such as trifluoromethylmercapto; hydroxy lower alkyl, such as hydroxymethyl or 1-hydroxymethyl; lower alkanesulfonyl, such as methanesulfonyl; halogen lower alkanesulfonyl, such as trifluoromethanesulfonyl; phenylsulfonyl; dihydroxybora (—B(OH)$_2$); lower alkylpyrimidinyl, such as 2-methylpyrimidin-4-yl; oxazolyl, such as oxazol-5-yl; lower alkyldioxolanyl, such as 2-methyl-1,3-dioxolan-2-yl; pyrazolyl, such as 1H-pyrazol-3-yl; lower alkylpyrazolyl, such as 1-methylpyrazol-3-yl; lower alkylenedioxy bonded to two adjacent carbon atoms, such as methylenedioxy; pyridyl; piperazinyl; lower alkylpiperazinyl; morpholinyl; phenylamino or phenyl lower alkylamino either unsubstituted or substituted in the phenyl moiety by halogen, lower alkyl, hydroxy, lower alkanoyloxy, lower alkoxy, carboxy, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or by trifluoromethyl; or a radical of formula $R_3$—$S(O)_m$—, wherein $R_3$ is lower alkyl and m is 0, 1 or 2. In a preferred embodiment of the invention, aryl which is substituted by one or more substituents is, in particular, lower alkylpiperazinylcarbonylphenyl, morpholinylcarbonylphenyl, N,N-di-lower alkylcarbamoylphenyl, lower alkylpiperazinyl lower alkylphenyl, morpholinyl lower alkylphenyl or N,N-di-lower alkylamino lower alkylphenyl.

Halogen is especially fluorine, chlorine, bromine, or iodine, in particular fluorine or chlorine.

Halogen lower alkyl is methyl or ethyl that is substituted in particular by halogen, such as fluorine or chlorine, especially methyl fluoride or also methyl chloride.

Hydroxy lower alkyl is in particular lower alkyl which is terminally substituted by hydroxy, preferably hydroxymethyl.

Heterocyclyl is preferably a wholly saturated, partly saturated or unsaturated radical and is preferably monocyclic, or also bi- or tricyclic; it preferably has 1 to 20, especially 1 to 14 ring atoms, whereby one or more, especially one to four, primarily one or two of the ring atoms present at least in the ring which is bonded to the remaining radical of the compound of formula I, and/or in further rings, where present, are hetero atoms selected especially from the group comprising nitrogen, oxygen and sulfur; whereby heteroaryl is unsubstituted or substituted by one or more substituents selected, independently of one another, from those named as substituents for aryl; and it is especially selected from the group comprising pyrrolidinyl, pyrrolinyl, imidazolinyl, imidazolidinyl, pyrazolidinyl, pyrazolinyl, piperidinyl, piperazinyl, indolinyl, isoindolinyl, quinuclidinyl, morpholinyl, thiomorpholinyl, chromanyl, isochromanyl, imidazolyl, thienyl, furyl, pyranyl, thianthrenyl, isobenzofuranyl, benzofuranyl, chromenyl, 2H-pyrrolyl, pyrrolyl, benzimidazolyl, pyrazolyl, thiazolyl, isothiazolyl, oxazolyl, isoxazolyl, pyridyl, pyrazinyl, pyrimidinyl, pyridazinyl, indolizinyl, isoindolyl, 3H-indolyl, indolyl, indazolyl, triazolyl, tetrazolyl, purinyl, 4H-quinolizinyl, isoquinolyl, quinolyl, phthalazinyl, naphthyridinyl, quinoxalyl, quinazolinyl, cinnolinyl, pteridinyl, carbazolyl, phenanthridinyl, acridinyl, perimidinyl, phenanthrolinyl and furazanyl, whereby these radicals may be unsubstituted or substituted by one to three, preferably one or two of the substituents named as substituents for aryl, which may be selected independently of one another. Q is most preferably pyridyl or indolyl.

Cycloalkyl is preferably $C_3$-$C_{12}$-, especially $C_3$-$C_8$-cycloalkyl, and is in particular cyclopropyl, cyclobutyl, cyclopentyl or cyclohexyl; and is unsubstituted or substituted by one or more, especially one to three, preferably one or two of the substituents named, independently of one another, as substituents for aryl.

Arylalkyl is preferably aryl lower alkyl, for example arylmethyl, whereby aryl is preferably defined as above and is unsubstituted or is substituted as described above.

Heterocyclylalkyl is preferably heterocyclyl lower alkyl, for example heterocyclylmethyl, whereby heterocyclyl is preferably defined as above and is unsubstituted or is substituted as described above.

Cycloalkylalkyl is preferably cycloalkyl lower alkyl, for example cycloalkylmethyl: whereby cycloalkyl is preferably defined as above and is unsubstituted or is substituted as described above.

A carbon atom which bears a radical A has the formula C(A).

Preference is given to compounds of formula I, wherein X signifies nitrogen. On the other hand, preference is also given to compounds of formula I, in which X signifies a carbon atom bearing a radical A, especially wherein X signifies CH.

Salts are primarily the pharmaceutically acceptable salts of compounds of formula I. Salts may be formed provided that salt-forming groups are present In a compound of formula I. Salts of compounds of formula I are in particular acid addition salts (if a basic group is present in the relevant compound of formula I, such as amino or imino), or salts with cations or bases (if an acidic group, such as carboxy, is present in the relevant compound of formula I); where several salt-forming groups are present, internal salts or mixed salts may also be present.

Such salts are formed, for example, as acid addition salts, preferably with organic or inorganic acids, from compounds of formula I with a basic nitrogen atom, especially the pharmaceutically acceptable salts. Suitable inorganic acids are, for example, hydrohalic acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, 2-hydroxybutyric acid, gluconic acid, glucose-monocarboxylic acid, fumaric acid, succinic acid, adipic acid, pimelic acid, suberic acid, azelaic acid, malic acid, tartaric acid, citric acid, glucaric acid, galactaric acid, amino acids, such as glutamic acid, aspartic acid, N-methylglycine, acetylaminoacetic acid, N-acetylasparagine or N-acetylcysteine, pyruvic acid, acetoacetic acid, phosphoserine, 2- or 3-glycerophosphoric acid, maleic acid, hydroxymaleic acid, methylmaleic acid, cyclohexanecarboxylic acid, benzoic acid, salicylic acid, 1- or 3-hydroxynaphthyl-2-carboxylic acid, 3,4,5-trimethoxybenzoic acid, 2-phenoxybenzoic acid, 2-acetoxybenzoic acid, 4-aminosalicylic acid, phthalic acid, phenylacetic acid, glucuronic acid, galacturonic acid, methane- or ethane-sulphonic acid, 2-hydroxyethanesulfonic acid, ethane-1,2-disulphonic acid, benzenesulphonic acid, 2-naphthalenesulphonic acid, 1,5-naphthalene-disulphonic acid, N-cyclohexylsulphamic acid, N-methyl-, N-ethyl- or N-propyl-sulphamic acid, or other organic protonic acids, such as ascorbic acid. Where acidic groups are present (for example carboxy), corresponding salts with suitable cation salts or bases may be present, such as non-toxic metal salts of groups Ia, Ib, IIa or IIb of the periodic table of elements, especially suitable alkali metal salts, such as lithium, sodium or potassium, or alkaline earth metal salts, such as magnesium or calcium salts, or zinc or ammonium salts, or also salts with organic amines, such as unsubstituted or substituted mono-, di- or trialkylamines, especially mono-, di- or tri-lower alkylamines, or with quaternary ammonium compounds, for example with N-Methyl-N-ethylamine, diethylamine, triethylamine, mono-, bis- or tris(2-hydroxy lower alkyl)amines, such as mono-, bis- or tris(2-hydroyethyl) amine, N,N-di-lower alkyl-N-(hydroxy lower alkyl)-amines, such as N,N-dimethyl-N-(2-hydroxyethyl)-amine or tri-(2-hydroxyethyl)-amine, or N-methyl-D-glucamine, or quaternary ammonium salts, such as tetrabutylammonium salts.

For isolation or purification purposes it is also possible to use pharmaceutically unacceptable salts, for example picrates or perchlorates. Only the pharmaceutically acceptable salts or free compounds not present as a salt (optionally in the form of pharmaceutical preparations) attain therapeutic use, and these are therefore preferred.

In view of the close relationship between the novel compounds in free form and in the form of their salts, including those salts that can be used as intermediates, for example in the purification or identification of the novel compounds, hereinbefore and hereinafter any reference to the free compounds is to be understood as referring also to the corresponding salts, as appropriate and expedient.

The compounds of formula I have valuable pharmacological properties. In particular they exhibit specific inhibitory activities that are of high pharmacological interest. They are preferably active as tyrosine kinase inhibitors and/or also as inhibitors of serine/threonine protein kinases. For example, they exhibit very good inhibitory action against the tyrosine activity of the receptor for epidermal growth factor (EGF) and the receptor of the vascular endothelial growth factor (VEGF). Furthermore, they show efficacy against a series of other tyrosine protein kinases, such as c-erbB2 kinase. The effects mediated by such specific enzyme activities play a key role in signal transmission in a large number of mammalian cells, including human cells, especially epithelial cells, cells of the immune system and cells of the central and peripheral nervous system. For example, the activation of the receptor-associated tyrosine protein kinase of the receptor for the epidermal growth factor EGF (EGF-R-TPK) is a prerequisite for cell division and thus for the proliferation of a given cell population. Thus, an increase in the concentration of EGF receptor-specific tyrosine protein kinase inhibitors inhibits cell proliferation. In a similar manner, an inhibition in the activity of the tyrosine protein kinases of the vascular endothelial growth factor VEGF (VEGF-R-TPK, e.g. KDR and Flt-1) effects reduced vessel formation and can thus contribute towards preventing the growth of tumours which is dependent on sufficient blood supply, as well as preventing the formation of metastases. A comparable effect applies also to other said kinases mentioned hereinbefore and hereinafter, and analogues thereof.

In addition to or instead of the inhibition of EGF receptor tyrosine protein kinase and/or the VEGF receptor kinase, compounds of formula I inhibit, to differing extents, other tyrosine protein kinases that are involved in signal transmission mediated by trophic factors, for example abl kinase, especially v-abl kinase, kinases from the family of src kinases, especially c-src kinase, lck, fyn; other kinases of the er EGF family, for example c-erbB2-kinase (HER-2), c-erbB3 kinase, c-erbB4 kinase; members of the family of PDGF receptor tyrosine protein kinases, for example PDGF receptor kinase, CSF-1 receptor kinase, Kit receptor kinase and FGF receptor kinase; the receptor kinase of the insulin-like growth factor (IGF-1 kinase), and/or serine/threonine kinases, for example protein kinase C or cdc kinases, all of which play a role in growth regulation and in transformation in mammalian cells, including human cells.

The inhibition of EGF receptor-specific tyrosine protein kinase (EGF-R-TPK) can be demonstrated using known methods, for example using the recombinant intracellular domain of the EGF-receptor [EGF-R ICD; see e.g. E. McGlynn et al., Europ. J. Biochem. 207, 265-275 (1992)]. Compared with the control without inhibitor, the compounds of formula I inhibit the enzyme activity by 50% ($IC_{50}$), for example in a concentration of from 0.001 to 100 µM, especially from 0.001 to 20 µM.

The above-mentioned inhibition of v-abl tyrosine kinase is determined by the methods of N. Lydon et al., Oncogene Research 5, 161-173 (1990) and J. F. Geissler et al., Cancer Research 52, 4492-4498 (1992). In those methods [Val$^5$]-angiotensin II and [γ-$^{32}$P]-ATP are used as substrates.

The inhibition of c-erbB2 tyrosine kinase (HER-2) can be determined, for example, in the same way as for EGF-R-TPK (see House et al., Europ. J. Biochem. 140, 363-367 [1984]). The c-erbB2 kinase can be isolated, and its activity determined, by means of protocols known per se, for example in accordance with T. Akiyama et al., Science 232, 1644 (1986).

The activity of the compounds of formula I on EGF-stimulated cellular tyrosine phosphorylation in the EGF-receptor can be determined in the human A431 epithelial carcinoma cell line by means of an ELISA (EGFR-ELISA) which is described in U. Trinks et al., J. Med. Chem. 37:7, 1015-1027 (1994).

The stimulation of resting BALB/c3T3 cells by EGF rapidly induces the expression of c-fos nRNS. By pretreating the cells with a compound of formula I prior to stimulation with EGF, the c-fos expression can be inhibited. This test procedure is likewise described in U. Trinks et al., J. Med. Chem. 37:7, 1015-1027 (1994).

Other assays for determining the inhibitory action against further kinases, for example those named above, such as kit, Flt-1 or also KDR, may be carried out using the respective tyrosine kinase, which can be used as the glutathione-S-transferase fusion protein using, for example, a baculovirus system. The respective fusion proteins are purified by chromatography using a glutathione-sepharose column, and used to determine the $IC_{50}$ values of the test compounds of formula I. With Flt-1 or KDR, $IC_{50}$ values in the range of 1 nM to 200 µM could be found, for example with KDR in the range of 100 nM to 100 µM.

In the micromolar range, for example, the compounds of formula I likewise also exhibit an inhibition in cell growth of EGF-dependent cell lines, such as the epidermoid BALB/c mouse keratinocyte cell line (see Weissmann, B. A., and Aaronson, S. A., Cell 32, 599 (1983)) or of the A431 cell line, which are recognised as useful standard sources of EGF-dependent epithelial cells (see Carpenter, G., and Zendegni, J. Anal. Biochem. 153, 279-282 (1985)). In a known test method [see Meyer at al, Int. J. Cancer 43, 851 (1989)], the inhibitory action of the compounds of formula I is determined in short as follows: BALB/MK cells (10,000/microtitre plate well) are transferred to 96-well microtitre plates. The test compounds (dissolved in DMSO) are added in a series of concentrations (dilution series), so that the final concentration of DMSO is no greater than 1% (v/v). After the addition, the plates are incubated for three days, during which time the control cultures without test substance may undergo at least three cell division cycles. The growth of MK cells is measured by methylene blue dyeing: After incubation, the cells are fixed with glutaraldehyde, washed with water and stained with 0.05% methylene blue. After one washing step, the dye is eluted with 3% HCl and the optical density per well of the microtitre plate is measured as 665 nm using a Titertek multiscan. $IC_{50}$ values are determined by a computer-aided system using the formula:

$$IC_{50}=[(OD_{test}-OD_{start})/(OD_{control}-OD_{start})]\times 100.$$

The $IC_{50}$ value in those experiments is given as that concentration of the test compound in question that results in a cell count that is 50% lower than that obtained using the control without inhibitor.

The compounds of formula I may effect inhibition of the growth of tumour cells also in vivo, as shown, for example, by the test described below: the test is based on inhibition of the growth of the human epidermold carcinoma A431 (ATCC No. CRL 1555; American Type Culture Collection, Rockville, Md., USA; see Santon, J. B., et al, Cancer Research 46, 4701-4705 (1986) and Ozawa, S., et al., Int. J. Cancer 40, 706-710 (1987)), which is transplanted into female BALB/c nude mice (Bomholtgard, Denmark). That carcinoma exhibits a growth that correlates with the extent of the expression of the EGF-receptor. In the experiment, tumours having a volume of approximately 1 cm³ cultured in vivo are surgically removed from experimental animals under sterile conditions. The tumours are comminuted and suspended in 10 volumes (w/v) of phosphate-buffered saline. The suspension is injected s.c. (0.2 ml/mouse in phosphate-buffered saline) into the left flank of the animals. Alternatively, 1×10⁶ cells from an in vitro culture in 0.2 ml of phosphate-buffered saline can be injected. Treatment with test compounds of formula I is started 5 or 7 days after the transplant, when the tumours have reached a diameter of 4-5 mm. Each respective active substance (in various doses for different animal groups) is administered once daily for 15 successive days. The tumour growth is determined by measuring the diameter of the tumours along two axes that are perpendicular to each other. The tumour volumes are calculated using the known formula $p×L×D^2/6$ (see Evans, B. D., et al., Brit. J. Cancer 45, 466-8 (1982)). The results are given as treatment/control percentages (T/C x 100=T/C %).

Alternatively to the cell line A-431, other cell lines may also be used to demonstrate the anti-tumour activity of compounds of formula I in vivo, for example:

the MCF-7 breast adenocarcinoma cell line (ATCC No. HTB 22; see also J. Natl. Cancer Inst. (Bethesda) 51, 1409-16 [1973]);

the MDA-MB 468 breast adenocarcinoma cell line (ATCC No. HTB 132; see also In Vitro 14, 911-15 [1978]);

the MDA-MB 231 breast adenocarcinoma cell line (ATCC No. HTB 26; see also J. Natl. Cancer Inst. (Bethesda) 53, 661-74 (1974));

the Colo 205 colon carcinoma cell line (ATCC No. CCL 222; see also Cancer Res. 38, 1345-55 [1978]);

the HCT 116 colon carcinoma cell line (ATCC No. CCL 247; see also Cancer Res. 41 1751-6 [1981]);

the DU145 prostate carcinoma cell line (ATCC No. HTB 81; see also Cancer Res. 37, 4049-58 [1978]); and the PC-3 prostate carcinoma cell line PC-3 (ATCC No. CRL 1435; see also Cancer Res. 40, 524-34 [1980]).

The efficacy of the compounds of formula I of the invention as inhibitors of VEGF receptor tyrosine kinase activity can be demonstrated as follows:

test for activity against VEGF-receptor tyrosine kinase. The test is conducted using Flt-1 VEGF-receptor tyrosine kinase. The detailed procedure is as follows: 30 µl kinase solution (10 ng of the kinase domain of Flt-1, Shibuya et al., Oncogene 5, 519-24 [1990]) in 20 mM Tris·HCl pH 7.6, 3 mM manganese dichloride ($MnCl_2$), 3 mM magnesium chloride ($MgCl_2$) and 3 µg/ml poly(Glu,Tyr) 4:1 (Sigma, Buchs, Switzerland), 8 µM [$^{33}$P]-ATP (0,2 µCi/batch), 1% dimethyl sulfoxide, and 0 to 50 µM of the compound to be tested are incubated together for 15 minutes at room temperature. Then, the reaction is ended by adding 10 µl of 0.25 M ethylenediamine tetraacetate (EDTA) pH 7. Using a "Multichannel Dispenser" (LAB SYSTEMS, USA), an aliquot of 20 µl is added to a PVDF-(=polyvinyl difluoride-) Immobilon P membrane (Millipore, USA), which is then incorporated into a Millipore microtitre filter manifold, and connected to a vacuum. After completely removing the solvent, the membrane is incubated four times in succession in a bath containing 0.5% phosphoric acid ($H_3PO_4$), each time for 10 minutes whilst shaking, then transferred to a Hewlett Packard TopCount Manifold, and the radioactivity measured after adding 10 µl Microscint® ((β-scintillation counter liquid; Packard USA). $IC_{50}$-values are determined by linear regression analysis of the percentages for the inhibition of each test compound in three concentrations (as a rule 0.01, 0.1, and 1 µM). Preferably, inhibiting concentrations ($IC_{50}$ with 50% of maximum inhibition compared with a control without inhibiting substance of formula I) in the range of 1 to 300 µM, especially in the range of 1 to 100 µM, are found.

The in vivo activity of a compound of formula I may also be demonstrated here using the above-described test with A-431 cells or other cell lines in mice.

The inhibition of VEGF-induced KDR-receptor autophosphorylation can be confirmed with a further in vitro experiment in cells: Transfected CHO cells, which permanently express human VEGF receptor KDR, are seeded in culture medium (with 10% fetal calf serum =FCS) in 6-well cell culture plates and incubated at 37° C., 5% $CO_2$ until they show about 80% confluency. The compounds to be tested are then diluted in culture medium (without FCS, with 0.1% bovine serum albumin) and added to the cells (controls comprise medium only without test compounds). After incubating for 2 hours at 37° C., recombinant VEGF is added; the resulting VEGF final concentration is 20 ng/ml. After incubating for a further five minutes at 37° C., the cells are washed twice with ice-cold PBS (phosphate-buffered physiological saline) and immediately lysed in 100 µl lysis buffer per batch. The lysates are then centrifuged to remove the cell nuclei, and the protein concentrations of the supernatants are determined using a commercial protein assay (BIORAD). The lysates can then either be immediately used or, if necessary, stored at −20° C.

A sandwich ELISA is carried out to measure the KDR-receptor phosphorylation. A KDR-specific monoclonal antibody (for example Mab 1495.12.14; prepared by H. Towbin) is adsorbed on black ELISA plates (OptiPlate™ HTRF-96 from Packard). The plates are then washed and the remaining free protein binding sites are saturated with 1% bovine serum albumin in PBS. The cell lysates (20 µg protein/batch) are then incubated overnight at 4° C. with an antiphosphotyrosine antibody ligated with alkaline phosphatase (PY20: AP from Transduction Laboratories). The binding of the antiphosphotyrosine antibody is then determined using a luminescent AP substrate (CDP-Star, ready to use, with Emerald II; TROPIX). Luminescence is measured in a Packard Top Count Microplate Scintillation Counter (Top Count). The difference between the signal from the positive control (stimulated with VEGF) and that from the negative control (not stimulated with VEGF) corresponds to the VEGF-induced KDR receptor phosphorylation (=100%). The activity of a test compound is calculated as the % inhibition of VEGF-induced KDR receptor phosphorylation, whereby the concentration of the compound that induces half the maximum inhibition is defined as the ED50 (effective dose for 50% inhibition).

The suitability of a compound of formula I for the treatment of arthritis, as an example of an inflammatory rheumatic or rheumatoid disease, may be proved as follows:

The known rat adjuvant arthritis model (Rat Adjuvant Arthritis Model; Pearson, Proc. Soc. Exp. Biol. 91, 95-101 (1956)) is used to demonstrate the anti-arthritic activity of a compound of formula I. Male Wistar rats (5 animals per group, weight ca. 200 g, acquired from Iffa Credo, France) are individually injected i.d. (intradermally) via the tail with 0.1 ml of mineral oil containing 0.6 mg of lyophilised heat-inactivated *Mycobacterium tuberculosis*. The rats are treated with test compound (3, 10 or 30 mg/kg p.o. once daily) or with the carrier material (water) from day 15 to day 22 (therapeutic dosage scheme). At the end of the experiment, swelling of the tarsal joints is measured by a micro-sliding gauge The percentage of each inhibition of the swelling of the paw is calculated by comparing the value of arthritic animals treated with carrier material (0% inhibition) and with healthy animals treated with carrier material (100% inhibition).

The effect of a compound of formula I on pain may be demonstrated in the following model for noci-reception. In the model, hyperalgesia which is caused by an intraplanar yeast injection is measured by using increasing pressure on the foot until the test animal cries out or removes the paw from the pressure cushion being applied. The model reacts to COX inhibitors, and diclofenac (3 mg/kg) is used as a positive control.

The baseline pressure which is required to induce a vocal sound or removal of the paw is determined individually (2 hours before treatment) on male Sprague-Dawley rats (weight ca. 180 g, acquired from Iffa Credo, France). Then, 100 µl of a 20% yeast suspension in water is injected into the hind paws. 2 hours after this, the rats are treated by oral administration with the test compound (3, 10 or 30 mg/kg) or with diclofenac (3 mg/kg) or with the carrier material (physiological saline) p.o. (point of time: nill), and the pressure test is repeated 1 and 2 hours after administration. Using the standard apparatus (Ugo Basile, Italy), the pressure needed to induce a vocal expression or removal of the paw is measured at these points in time on animals treated with the test compound and compared with those treated with only the carrier material.

As a result of their above-mentioned properties, for example as inhibitors of VEGF- or EGF-receptor tyrosine kinase, the compounds of formula I are suitable especially for treating inflammatory rheumatic or rheumatoid diseases, in particular their manifestation on the locomotor system, for example inflammatory rheumatoid diseases such as polyarthritis, and/or for treating pain.

On the basis of their efficacy as inhibitors of VEGF receptor kinase activity, the compounds of formula I inhibit in particular the growth of blood vessels, and are thus, for example, effective against a series of diseases associated with deregulated angiogenesis, especially diseases caused by ocular neovascularisation, such as diabetic retinopathy or age-induced macula degeneration; psoriasis, haemangioblastoma, sich as haemangioma; proliferative diseases of mesangial cells, such as chromic or acute renal diseases, for example diabetic nephropathy, malignant nephrosclerosis, thrombotic microangiopathy syndrome, transplant rejection, or especially inflammatory renal diseases, such as glomerulonephritis, especially mesangioproliferative glomerulonephritis, haemolytic uremic syndrome, diabetic nephropathy or hypertensive nephrosclerosis; atheroma, arterial restenosis; autoimmune diseases, acute inflammation, fibrotic diseases (for example cirrhosis of the liver), diabetes, endometriosis, chronic asthma, arterial or post-transplantational atherosclerosis, neurodegenerative diseases and in particular neoplastic diseases (solid tumours, and also leukaemia and other "liquid" tumours, especially those that express c-kit, KDR or flt-1), such as, in particular, breast cancer, colon cancer, lung cancer (especially small-cell lung cancer), cancer of the prostate, Kaposi's sarcoma, CNS tumours, ovarian cancer, renal tumours or VHL tumours. A compound of formula I inhibits the growth of tumours and is especially suitable for preventing the metastatic spread of tumours and the growth of micrometastases.

Owing to their efficacy as inhibitors of tyrosine kinase activity of the receptor for the epidermal growth factor (EGF) or of the other tyrosine protein kinases mentioned, the compounds of formula I are especially useful in the treatment of benign or malignant tumours. They are capable of effecting tumour regression and of preventing the formation of tumour metastases and the growth of micrometastases. They can be used especially in the case of epidermal hyperproliferation (psoriasis), in the treatment of neoplasias of epithelial character, e.g. mammary carcinomas, and in leukaemias. Furthermore, the compounds of formula I may be used to treat diseases of the immune system, provided that several or preferably single tyrosine protein kinase(s) and/or (furthermore) serine/threonine protein kinase(s) is/are involved; the compounds of formula I may also be used in the treatment of disorders of the central or peripheral nervous system in which signal transmission by several or, preferably, a single tyrosine protein kinase(s) and/or (furthermore) serine/threonine protein kinase(s) islare involved.

In general, the present invention relates also to the use of the compounds of formula I in the inhibition of the mentioned protein kinases.

The inhibition of proliferation for example of tumour cells or epithelial cells in the case of psoriasis, can under certain circumstances be based on the inhibition of one or more of the said kinases, or further unknown mechanisms may also exist.

The compounds according to the invention can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. In particular, a compound of formula I can be administered for example in the case of tumour therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumour regression, or even chemopreventive therapy, for example in patients at risk.

Therapeutic agents for possible combination are especially one or more antiproliferative, cytostatic or cytotoxic compounds, for example a chemotherapeutic agent or several agents selected from the group which includes, but is not limited to, an inhibitor of polyamine biosynthesis, an inhibitor of a protein kinase, especially of a serine/threonine protein kinase, such as protein kinase C, or of a tyrosine protein kinase, such as the EGF receptor tyrosine kinase, e.g. PKI166, the VEGF receptor tyrosine kinase, e.g. PTK787, or the PDGF receptor tyrosine kinase, e.g. ST1571, a cytokine, a negative growth regulator, such as TGF-1 or IFN-13, an aromatase inhibitor, e.g. letrozole or anastrozole, an inhibitor of the interaction of an SH2 domain with a phosphorylated protein, antiestrogens, topoisomerase I inhibitors, such as irinotecan, topoisomerase II inhibitors, microtubule active agents, e.g. paclitaxel, discodermolide or an epothilone, alkylating agents, antineoplastic antimetabolites, such as gemcitabine or capecitabine, platin compounds, such as carboplatin or cisplatin, anti-angiogenic compounds, gonadorelin agonists, anti-androgens, bisphosphonates, e.g. AREDIA® or ZOMETA®, and trastuzumab. The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

PREFERRED EMBODIMENTS OF THE INVENTION

In the following preferred embodiments of the invention, general definitions, independently of one another, can be replaced by the preferred definitions named above or below, whereby the resulting embodiments of the invention are the preferred ones.

Preference is given to a compound of formula I, wherein X signifies either nitrogen or a carbon atom bearing a radical A; A signifies hydrogen or —COOW, wherein W signifies alkyl or hydrogen; Y is NR', S or O, wherein R' signifies hydrogen or alky; R signifies alkyl, aryl, heterocyclyl, cycloalkyl, arylalkyl, heterocyclylalkyl or cycyoalkylalkyl, whereby each of these radicals is unsubstituted or substituted; or COOR', COR' or CONR'R", wherein R' and R", independently of one another, are hydrogen or alkyl, aryl, heterocyclyl, cycloalkyl, arylalkyl, heterocyclylalkyl or cycloalkylalkyl, whereby each of these radicals is unsubstituted or substituted; and Q is aryl, aryl lower alkyl or heterocyclyl, which are respectively unsubstituted or substituted; as well as a salt thereof.

A compound of formula I, wherein X signifies either nitrogen or a carbon atom bearing a radical A; A signifies hydrogen or —COOW, wherein W signifies alkyl or hydrogen; Y is NR', S or O, whereby R' signifies hydrogen or alkyl; R signifies aryl; and Q is aryl, aryl lower alkyl or heterocyclyl, which are respectively unsubstituted or substituted, is very preferred; as well as a salt thereof.

The invention relates in particular to a compound of formula I, wherein X signifies either nitrogen (preferred) or a carbon atom bearing a radical A;

A signifies hydrogen or —COOW, wherein W signifies alkyl, especially lower alkyl, or hydrogen; R signifies aryl; and Q signifies aryl; or a salt thereof.

Preference is given to a compound of formula I wherein X signifies either nitrogen or a carbon atom bearing a radical A; A signifies hydrogen; R is phenyl which is substituted by nitro or amino; and Q is phenyl which is substituted by one or more radicals (especially 1 or 2 radicals), which, independently of one another, are selected from hydroxy, lower alkoxy, especially methoxy, and halogen, especially chlorine or bromine; or a salt thereof.

Further preferred is a compound of formula I, wherein X signifies either nitrogen or a carbon atom bearing a radical A; A signifies hydrogen; R signifies aryl; and Q signifies aryl, aryl lower alkyl or heterocyclyl; or a salt thereof; whereby aryl is phenyl, naphthyl, fluorenyl or phenanthrenyl, which are respectively unsubstituted or substituted by up to three substituents selected from amino; lower alkylamino; N,N-di-lower alkylamino; amino lower alkyl; lower alkylamino lower alkyl; N,N-di-lower alkylamino lower alkyl; lower alkanoylamino; halogen; lower alkyl; lower alkenyl; phenyl; naphthyl; halogen lower alkyl; hydroxy; lower alkoxy; lower alkenyloxy; phenyl lower alkoxy; lower alkanoyloxy; carbamyl lower alkoxy; carboxy lower alkoxy; phenyl lower alkoxycarbonyl lower alkoxy; mercapto, nitro; carboxy; lower alkoxycarbonyl; phenyl lower alkoxycarbonyl; cyano; $C_8$-$C_{12}$-alkoxy; carbamoyl; lower alkylcarbamoyl; N,N-di-lower alkylcarbamoyl; N-mono- or N,N-diphenyl lower alkyl-carbamoyl; lower alkanoyl; phenyloxy; halogen lower alkyloxy; lower alkoxycarbonyl; lower alkylpiperazinylcarbonyl; morpholinylcarbonyl; lower alkylpiperazinyl lower alkyl; morpholinyl lower alkyl; lower alkyl mercapto; halogen lower alkylmercapto; hydroxy lower alkyl; lower alkanesulfonyl; halogen lower alkanesulfonyl; phenylsulfonyl; dihydroxybora; lower alkyl-pyrimidinyl; oxazolyl; lower alkyldioxolanyl; pyrazolyl; lower alkylpyrazolyl; lower alkylene-dioxy bonded to two adjavent carbon atoms; pyridyl; piperazinyl; lower alkylpiperazinyl; morpholinyl; phenylamino or phenyl lower alkylamino either unsubstituted or substituted in the phenyl moiety by halogen, lower alkyl, hydroxy, lower alkanoyloxy, lower alkoxy, carboxy, lower alkoxycarbonyl, carbamoyl, N-lower alkylcarbamoyl, N,N-di-lower alkylcarbamoyl, cyano, amino, lower alkanoylamino, lower alkylamino, N,N-di-lower alkylamino or trifluoromethyl; or a radical of formula $R_3$-S(O)$_m$-, wherein $R_3$ is lower alkyl and m is 0, 1 or 2.

Special preference is given to a compound of formula I wherein X signifies either nitrogen or a carbon atom bearing a radical A; A signifies hydrogen; R is phenyl which is substituted by amino; especially 4-aminophenyl; and Q is phenyl which is substituted by one or more radicals—especially 1 or 2 radicals—, which are selected, independently of one another, from hydroxy, lower alkoxy, especially methoxy, and halogen, especially chlorine or bromine.

Particular preference is given to a compound of formula I, wherein X signifies either nitrogen or a carbon atom bearing a radical A; wherein A signifies hydrogen; R is phenyl which is substituted by nitro, amino, lower alkylpiperazinylcarbonyl, morpholinylcarbonyl, N,N-di-lower-alkylcarbamoyl, N,N-di-lower alkylamino lower alkyl, lower alkylpiperazinyl lower alkyl or morpholinyl lower alkyl; and Q is benzyl, phenylethyl; phenyl which is unsubstituted or is substituted by one or more radicals, which independently of one another, are selected from hydroxy, lower alkyl, lower alkoxy and halogen; pyridyl which is substituted by hydroxy or lower alkoxy; or indolyl which is substituted by halogen and lower alyl, as well as a salt thereof.

Also especially preferred is a compound of formula I, wherein Y is NH (imino).

A compound selected from the compounds of formula I named in the examples, or a salt thereof, provided that at least one salt-forming group is present, is very preferred.

Preparation Process

In the following processes, if not otherwise stated, the symbols R, A, Q, X and Y respectively have the significances named for the compounds of formula I, whereby significances indicated as preferred in the starting materials are likewise preferred.

Compounds of formula I, or salts thereof, may be prepared by known processes, which are however new to these compounds, especially whereby a) a compound of formula II,

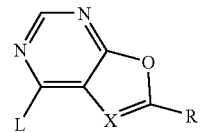

(II)

wherein X and R have the significances given for a compound of formula I and L signifies a leaving group, e.g. chloride, are reacted with an amine, a phenol or thiole of formula III,

Q-YH (III)

wherein Q has the significances given for compounds of formula I and Y is NR', S or O, whereby R' signifies hydrogen or alkyl; wherein, if necessary, functional groups present in a compound of formula II and/or III, which are not to take part in the reaction, are present in protected form, and protecting groups that are present are cleaved;

and, if desired, an obtainable compound of formula I is converted into a different compound of formula I; an obtainable free compound of formula I is converted into a salt; an obtainable salt of a compound of formula I is converted into another salt or the free compound of formula I; and/or obtainable isomeric mixtures of compounds of formula I are separated into the individual isomers;

Detailed Description of the Process

A compound of formula II or III may be present in free form, or if the reaction of functional groups which should not participate in the reaction is to be prevented, in a form in which the functional groups that do not participate are protected.

If one or more other functional groups, for example hydroxy, carboxy, amino, or mercapto, etc., are or need to be protected in a compound of formulae II, because they should not take part in the reaction, the protecting groups are those that are usually used in the synthesis of peptide compounds, and also of cephalosporins and penicillins, as well as nucleic acid derivatives and sugars. These protecting groups may already be present in precursors and should protect the functional groups concerned against unwanted secondary reactions, such as acylations, etherifications, esterifications, oxidations, solvolysis, and similar reactions. The protecting groups for functional groups in starting materials whose transformation should be avoided, include especially the conventional protecting groups that are normally used in the synthesis of peptide compounds, cephalosporins, penicillins or nucleic acid derivatives and sugars. In certain cases, the protecting groups may, in addition to this protection, effect a selective, for example stereoselective, course of reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end products.

A person skilled in the art knows, or can easily establish, which protecting groups are suitable for the reactions mentioned hereinabove and hereinafter. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1991, in T. W. Greene, P. G. M. Wuts, "Protective Groups in Organic Synthesis", 2$^{nd}$ edition, John Wiley & Son Inc., 1981, in "The Peptides"; Volume 3 (: E. Gross and J. Meienhofer), Academic Press, London and New York 1981, in "Methoden der organischen Chemie" (*Methods of organic chemistry*), Houben Weyl, 4th edition, Volume 15/l, Georg Thieme Verlag, Stuttgart 1974, in H.-D. Jakubke and H. Jescheit, "Aminosäuren, Peptide, Proteine" (*Amino acids, peptides, proteins*), Veriag Chemie, Weinheim, Deerfield Beach, and Basel 1982, and in Jochen Lehmann, "Chemie der Kohlenhydrate: Monosac charide und Derivate", (*Chemistry of carbohydrates: monosaccharides and derivatives*) Georg Thieme Verlag, Stuttgart 1974.

A leaving group in a compound of formula II is preferably halogen, especially bromine, or primarily chlorine or iodine. Other leaving groups are conceivable, e.g. aryl- or alkylsulfonyl groups, e.g. 4-toluenesulfonyl.

The reaction between the compound of formula II and an amine of formula III (Y=NR') preferably takes place in a suitable polar solvent, especially in an alcohol, especially lower alkanol, such as methanol, propanol, isopropanol or in particular ethanol or n-butanol, or mixtures thereof, or in a melt without the addition of solvents, especially if one of the reactants is present in liquid form; at elevated temperature, preferably between ca. 60° C. and reflux temperature of the relevant reaction mixture, for example under reflux, or at a temperature of between about 70 and 120° C. The compound of formula III may also be present as a salt, for example as an acid addition salt with a strong acid, such as a hydrogen halide, e.g. the salt of hydrogen chloride, or the relevant acid may be added to the reaction mixture, for example in the presence of a suitable solvent, such as an ether, e.g. dioxane. If L is iodine, the reaction is preferably effected in an inert solvent, such as toluene, in the presence of a base, especially an alkali metal carbonate, such as dipotassium carbonate, in the presence of catalytic amounts of an appropriate noble metal catalyst complex, such as tetrakis-(triphenylphosphine)-palladium, at an elevated temperature, especially between 80 and 115° C.

The reaction between the compound of formula II and a phenol of formula III (Y=O) preferably takes place in the presence of copper salts instead of under the conditions of the Ullmann ether synthesis, as described in Russ. Chem. Rev. 43, 679-689 (1974). In some cases, the reaction can be accomplished by heating the compounds of formula II and formula III (Y=O) in the presence of a base, like potassium carbonate, in a suitable solvent, e.g. dimethylformamide.

The reaction between the compound of formula II and a thiole of formula III (Y=S) preferably takes place in known manner in a polar solvent, such as dimethylformamide, dimethyl sulfoxide or HMPT, if necessary in the presence of an appropriate catalyst, such as the palladium complex tetrakis-(triphenylphosphine)-palladium(O).

Reactions

In the additional process steps, carried out as desired, functional groups of the starting compounds which should not take part in the reaction may be present in unprotected form or may be protected for example by one or more of the protecting groups mentioned hereinabove under process a). The protecting groups are then wholly or partly removed according to one of the methods described under process a).

Compounds of formula I, in which a nitro group is present as a substituent in an aryl radical, may be reacted by hydrogenation into the corresponding compound, in which an amino group is present instead of the nitro group. Hydrogenation in this case is effected either with elementary hydrogen ($H_2$) in the presence of an appropriate catalyst, for example a Raney catalyst, such as Raney nickel or Raney cobalt, in an appropriate solvent or solvent mixture, such as an ether, e.g. tetrahydrofuran, and/or a di-lower alkyl-imidazolidinone, such as 1,3-dimethyl-2-imidazolidinone (DMEU), preferably at temperatures of between 0 and 50° C., for example at room temperature, whereby the pressure may be raised or lowered, preferably at normal pressure; or with nascent hydrogen, for example produced by the reaction of a tin(II) salt, such as tin(II) chloride, in an appropriate solvent, such as an alcohol, e.g. ethanol, propanol or butanol, at preferred temperatures between 10° C. and reflux temperature of the reaction mixture, preferably at temperatures between room temperature and 80° C.

Salts of a compound of formula I with a salt-forming group may be prepared in a manner known per se. Thus, acid addition salts of compounds of formula I may be obtained e.g. by treatment with an acid or a suitable anion exchange reagent, and salts with cations e.g. by treatment with a metal salt, a base or a cation exchanger. Salts can usually be converted to free compounds, e.g. in the case of acid addition salts by treating with a suitable basic agent, for example with alkali metal carbonates, -hydrogen carbonates, or -hydroxides, e.g. potassium carbonate or sodium hydroxide, or in the case of salts, with bases.

Stereoisomeric mixtures, e.g. mixtures of diastereoisomers, can be separated into their corresponding isomers in a manner known per se by means of suitable separation methods. Diastereoisomeric mixtures may be separated into their individual diastereoisomers by means of fractionated crystallisation, chromatography, solvent distribution, and similar procedures. This separation may take place either at the stage of one of the starting compounds or in a compound of formula I itself. Enantiomers may be separated through the formation of diastereoisomeric salts, for example with an enantiomer-pure chiral acid, or by means of chromatography, for example by HPLC, using chromatographic substrates with chiral ligands.

Compounds of formula I, in which R is a group phenyl-C(=O)—O-lower alkyl, especially a group phenyl-C(=O)—O-methyl, may be converted into compounds of formula I, in which R is a group phenyl-C(=O)—O—H, for example by hydrolysis in the presence of an appropriate base, e.g. UOH, if necessary in the presence of an appropriate solvent, for example dioxane. This free acid of formula I may serve as an educt for the preparation of other derivatives, especially carboxylic acid esters and carboxylic acid amides, using processes that are known in literature. A carboxylic acid amide of this type, i.e. a compound of formula I, in which R is a group phenyl-C(=O)—NR'R'', may be converted by known manner into a compound of formula I, in which R is a group phenyl-$CH_2$—NR'R'', by means of a reaction with an appropriate reduction agent, e.g. diisobutyl aluminium hydride in tetrahydrofuran.

General Process Conditions

All process steps described here can be carried out under known reaction conditions, preferably under those specifically mentioned, in the absence of or usually in the presence of solvents or diluents, preferably those that are inert to the reagents used and able to dissolve them, in the absence or presence of catalysts, condensing agents or neutralisiing agents, for example ion exchangers, typically cation exchangers, for example in the $H^+$ form, depending on the type of reaction and/or reactants at reduced, normal, or elevated temperature, for example in the range from −100° C. to about 190° C., preferably from about −80° C. to about 150° C., for example at −80 to 60° C., at room temperature, at −20 to 40° C. or at the boiling point of the solvent used, under atmospheric pressure or in a closed vessel, if need be under pressure, and/or in an inert, for example an argon or nitrogen, atmosphere.

Salts may be present in all starting compounds and intermediates, if these contain salt-forming groups. Salts may also be present during the reaction of such compounds, provided that the reaction is not thereby disturbed.

At all reaction stages, isomeric mixtures that occur can be separated into their individual isomers, e.g. diastereoisomers or enantiomers, or into any mixtures of isomers, e.g. racemates or diastereoisomeric mixtures, typically as described under "Additional process steps".

In certain cases, typically in dehydrogenation or aldol reactions, it is possible to achieve stereoselective reactions, allowing for example easier recovery of individual isomers.

The solvents from which those can be selected which are suitable for the reaction in question include for example water, esters, typically lower alkyl-lower alkanoate, e.g diethyl acetate, ethers, typically aliphatic ethers, e.g. diethylether, or cyclic ethers, e.g. tetrahydrofuran, liquid aromatic hydrocarbons, typically benzene or toluene, alcohols, typically methanol, ethanol or 1- or 2-propanol, nitriles, typically acetonitrile, halogenated hydrocarbons, typically dichloromethane, acid amides, typically dimethylformamide, bases, typically heterocyclic nitrogen bases, e.g. pyridine, carboxylic acids, typically lower alkanecarboxylic acids, e.g. acetic acid, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process. Such solvent mixtures may also be used in working up, for example by chromatography or partitioning.

The invention relates also to those embodiments of the process in which one starts from a compound obtainable at any stage as an intermediate and carries out the missing steps, or breaks off the process at any stage, or forms a starting material under the reaction conditions, or uses said starting material in the form of a reactive derivative or salt, or produces a compound obtainable by means of the process according to the invention under those process conditions, and further processes the said compound in situ. In the preferred embodiment, one starts from those starting materials which lead to the compounds described hereinabove as preferred, particularly as especially preferred, primarily preferred, and/or preferred above all.

In the preferred embodiment, a compound of formula I is prepared according to the processes and process steps defined in the examples.

The compounds of formula I, including their salts, are also obtainable in the form of hydrates, or their crystals may include for example the solvent used for crystallisation (present as solvates).

Pharmaceutical Preparations Methods and Uses

The present invention relates also to pharmaceutical preparations that contain a compound of formula I as active ingredient and that can be used especially in the treatment of the diseases mentioned at the beginning. Preparations for enteral administration, such as nasal, buccal, rectal or, especially, oral administration, and for parenteral administration, such as intravenous, intramuscular or subcutaneous administration, to warm-blooded animals, especially humans, are especially preferred. The preparations contain the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The invention relates also to pharmaceutical preparations for use in a method for the prophylactic or especially therapeutic treatment of the human or animal body, especially against one of the above-mentioned diseases, to a process for the preparation thereof (especially in the form of compositions for the treatment of tumours) and to a method of treating the above-mentioned diseases, primarily tumour diseases, especially those mentioned above.

The invention relates also to processes and to the use of compounds of formula I for the preparation of pharmaceutical preparations which contain compounds of formula I as active component (active ingredient).

Preference is given to a pharmaceutical composition that is suitable for administration to a warm-blooded animal, especially a human or commercially useful mammal, suffering from a disease that is responsive to the inhibition of tyrosine or also serine/threonine protein kinase, for example psoriasis or especially a tumour disease, comprising a correspondingly effective amount of a compound of formula I, or a pharmaceutically acceptable salt thereof when salt-forming groups are present, together with at least one pharmaceutically acceptable carrier.

A pharmaceutical composition for the prophylactic or in particular therapeutic treatment of a disease that is responsive to the inhibition of tyrosine or also serine/threonine protein kinase, especially tumour diseases and other proliferative diseases of warm-blooded animals, especially humans, or of a commercially useful mammal requiring such treatment, especially one suffering from a disease of this type, containing a new compound of formula I, or a pharmaceutically acceptable salt thereof, as active ingredient in an amount that is prophylactically or especially therapeutically effective against said diseases, is likewise preferred.

Pharmaceutical preparations contain from about 0.000001% to 95% of the active ingredient, whereby single-dose forms of administration preferably have from approximately 0.00001% to 90% and multiple-dose forms of administration preferably have from approximately 0.0001 to 0.5% in the case of preparations for parenteral administration or 1% to 20% active ingredient in the case of preparations for enteral administration. Unit dose forms are, for example, coated and uncoated tablets, ampoules, vials, suppositories or capsules. Further dosage forms are, for example, ointments, sprays, etc. Examples are capsules containing from about 0.0002 g to about 1.0 g active ingredient.

The pharmaceutical preparations of the present invention are prepared in a manner known per se, for example by means of conventional mixing, granulating, coating, dissolving or lyophilising processes.

Preference is given to the use of solutions of the active ingredient, and also suspensions or dispersions, especially isotonic aqueous solutions, dispersions or suspensions which, for example in the case of lyophilised preparations which contain the active ingredient on its own or together with a carrier, for example mannitol, can be made up before use.

Pharmaceutical compositions for oral administration can be obtained, for example, by combining the active ingredient with one or more solid carriers, if need be granulating a resulting mixture, and processing the mixture or granules, if desired, to form tablets or tablet cores, if need be by the inclusion of additional excipients.

Suitable carriers are especially fillers, such as sugars, cellulose preparations and/or calcium phosphates, for example tricalcium phosphate or calcium hydrogen phosphate, and also binders, such as starches, methylcellulose, hydroxypropyl methylcellulose, sodium carboxymethylcellulose, and/or polyvinylpyrrolidone, and/or, if desired, disintegrants, such as the above-mentioned starches, also carboxymethyl starch, crosslinked polyvinylpyrrolidone, alginic acid or a salt thereof, such as sodium alginate.

Orally administrable pharmaceutical compositions also include hard capsules consisting of gelatin, and also soft, sealed capsules consisting of gelatin and a plasticiser, such as glycerol or sorbitol. The hard capsules may contain the active ingredient in the form of granules, for example in admixture with fillers, such as corn starch, binders, and/or glidants, such as talc or magnesium stearate, and if need be stabilisers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilisers and detergents may also be added.

Suitable rectally administrable pharmaceutical preparations are, for example, suppositories that consist of a combination of the active ingredient and a suppository base. Suitable suppository bases are, for example, natural or synthetic triglycerides, paraffin hydrocarbons, polyethylene glycols or higher alkanols.

The formulations suitable for parenteral administration are primarily aqueous solutions [for example in physiological saline, obtainable by diluting solutions in polyethylene glycol, such as polyethylene glycol (PEG) 300 or PEG 400] of an active ingredient in water-soluble form, e.g. a water-soluble salt, or aqueous injectable suspensions containing viscosity-increasing agents, e.g. sodium carboxymethyl cellulose, sorbitol and/or dextran, and where appropriate stabilizers.

Solutions such as those used, for example, for parenteral administration can also be employed as infusion solutions.

The invention similarly relates to a process or a method for the treatment of one of the above-mentioned pathological conditions, especially a disease which responds to an inhibition of tyrosine- or also serine/threonine protein kinase, especially a corresponding tumour disease. A compound of formula I can be administered as such or in the form of pharmaceutical compositions, prophylactically or therapeutically, preferably in an amount effective against the said diseases, to a warm-blooded animal, for example a human, requiring such treatment, the compounds especially being used in the form of pharmaceutical compositions. In the case of an individual having a bodyweight of about 70 kg the dose administered is from approximately 0.1 mg to approximately 5 g, preferably from approximately 0.5 mg to approximately 2000 mg, of a compound of the present invention. Administration takes place once or several time daily, for example 1 to 3 times daily, or at intervals, preferably e.g. every 1 to 4 weeks, for example weekly, every two weeks, every three weeks or every four weeks.

The present invention also relates in particular to the use of a compound of formula I, or a pharmaceutically acceptable salt thereof, especially a compound of formula I named as a preferred compound, or a pharmaceutically acceptable salt thereof, as such or in the form of a pharmaceutical formulation containing at least one pharmaceutically employable carrier, for the therapeutical and also prophylactic treatment of one or more of the above diseases.

The present invention also relates in particular to the use of a compound of formula I, or a pharmaceutically acceptable salt thereof, especially a compound of formula I named as a preferred compound, or a pharmaceutically acceptable salt thereof, for the preparation of a pharmaceutical formulation for the therapeutic and also prophylactic treatment of one or more of the above diseases.

The preferred dose quantity, composition, and preparation of pharmaceutical formulations (medicines) which are to be used in each case are described above.

Starting Materials

The starting materials of formulae II are known, are commercially available or may be produced analogously to known processes, whereby if necessary, protecting groups may also be introduced, used and cleaved again at appropriate times, analogously to the manner described above.

The starting materials of formula II may be produced by known processes, or they are known or are commercially available.

In particular, compounds of formula II, wherein X signifies nitrogen and the remaining radicals are defined as mentioned, may be produced by the following process.

By reacting a hydroxyaminopyrimidine compound of formula IV,

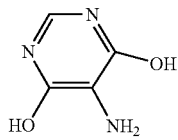
(IV)

with a reactive derivative of a carboxylic acid of formula V,

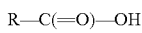 (V)

wherein R has the significances given for compounds of formula I, in an appropriate solvent or solvent mixture, for example in a tertiary nitrogen base, such as pyridine, preferably in the absence of oxygen, for example under an inert gas such as argon, at an elevated temperature, for example of 30° C. to reflux temperature of the reaction mixture, especially at reflux temperature.

A compound of formula VI is thereby obtained,

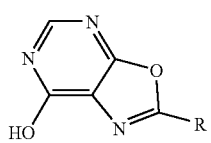
(VI)

wherein R has the significances given for compounds of formula I.

A reactive derivative of a carboxylic acid of formula V is understood to be in particular a corresponding acid halide, for example a corresponding acid chloride of formula R—(C═O)Cl, wherein R has the significances given for compounds of formula I. Such reactive carboxylic acid derivatives are known, may be produced according to or analogously to known processes, or are commercially available.

The compound of formula VI thus obtainable is then further reacted directly in situ or after isolation with a reagent which introduces the leaving group L, for example a compound selected from the compounds having formulae VII and VIII,

 (VII)

 (VIII)

wherein L has the significances given for compounds of formula II, especially with a phosphoryl halide such as phosphoryl chloride, or a sulfonyl halide such as sulfonyl chloride, whereby when introducing the leaving group L, instead of the hydroxy group of the compound of formula VI, the corresponding compound of formula II is obtained.

The reaction takes place especially in an appropriate solvent or solvent mixture, for example in a tertiary nitrogen base, such as pyridine, preferably in the absence of oxygen, for example under an inert gas such as argon, at an elevated temperature, for example of 30° C. to reflux temperature of the reaction mixture, especially at reflux temperature.

Where necessary, functional groups in the starting materials are also protected by protecting groups, and protecting groups that are present are removed at an appropriate time. The protecting groups used, their introduction and cleavage are described as above for the production of compounds of formula I.

Compounds of formula II, wherein X is a carbon atom bearing a radical A, may be produced by the following process:

A β-keto ester of formula IX,

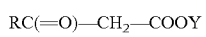 (IX)

wherein R has the significances given under formula I, and Y is alkyl, especially lower alkyl, e.g. ethyl, is transformed with a thionyl halide such as thionyl chloride, into a compound of formula X,

 (X)

wherein R and Y have the significances given under formula IX, and Hal is halogen, especially chlorine; the reaction takes place under known conditions (see e.g. J. Heterocycl. Chem. 22, 1621-1630 (1985)).

Subsequently, the compound of formula X is reacted with an alkali metal salt of formula XI

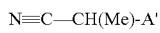 (XI)

wherein Me is an alkali metal, especially sodium, and A' signifies a radical —COOW, wherein W signifies alkyl (preferably; especially lower alkyl, such as ethyl), aryl, heterocyclyl or cycloalkyl, whereby each of these radicals is unsubstituted or substituted, under conventional conditions (see e.g. Chem. Ber. 95, 307-318 (1962)), thereby producing a compound of formula XII,

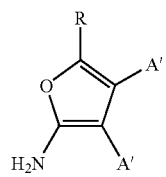
(XII)

wherein R has the significances given for compounds of formula I, and A' is defined as under formula XI.

The compound of formula XII is subsequently transformed, in the presence of a suitable solvent or solvent mixture, for example a di-lower alkyl carboxylic acid amide, such as dimethylformamide, with formamide in the presence of formic acid, at elevated temperatures, for example in the range of 100 to 150° C., if required under pressure, into a compound of formula XIII,

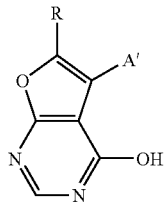

(XIII)

wherein R and A' have the significances given under formula XII.

Subsequently, a leaving group L, as defined under formula II, is introduced under analogous conditions to those described above for the transformation of a compound of formula VI into a compound of formula II, whereby a compound of formula II* is obtained, which falls within formula II:

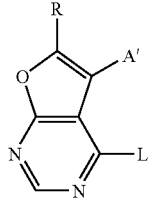

(II*)

In formula II*, A' and R have the significances given under formula XII, while L signifies a leaving group, preferably halogen, especially chlorine.

In order to obtain therefrom a compound of formula II, in which Y is a carbon atom bearing a radical A, which signifies hydrogen, it is necessary for saponification and decarboxylation to take place in accordance with known methods (see for example for saponification Chem. Ber. 95, 307-318 (1962), for decarboxylation Helv. Chim. Acta 33, 130 (1950) oder Bull. Soc. Chim. Fr. 1987, 339-349), for example under conditions such as those described under example 8a2. A compound of formula II** is thus obtained,

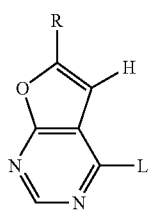

which likewise falls under formula II, and wherein R and L have the significances given for compounds of formula I.

It is also possible to decarboxylate a compound of formula XIII, in order to subsequently introduce the leaving group L by the said reagents, whereby a compound of formula II** is similarly obtained.

The compound of formula IV may be produced from 4,6-dihydroxy-5-nitropyrimidine (Aldrich, Buchs, Switzerland), for example by reduction with tin(II) chloride according to M. Ishidate et al., Chem. Pharm. Bull., 137-139 (1960). β-keto esters of formula IX are likewise known, may be produced by known processes or are commercially available.

EXAMPLES

The following examples illustrate the invention, but are not intended to restrict their scope in any way.

If not otherwise stated, all the IR spectra are measured in KBr. NMR: *) classification based on estimates. The melting points are uncorrected. The volume ratios of solvents or eluants are given in volume proportions (v/v). If not otherwise stated, the temperatures are given in degrees Celsius (° C.). Unless otherwise indicated, the reactions take place at room temperature.

| Abbreviations: | |
|---|---|
| Anal calc. | theoretical proportions of the elements in elementary analysis |
| TLC | thin-layer chromatography |
| DMEU | 1,3-dimethyl-2-imidazolidinone |
| DMF | dimethylformamide |
| Et | ethyl |
| EtOAc | ethyl acetate |
| found | found (=measured) proportions of the elements in elementary analysis: |
| h | hour(s) |
| HV | high vacuum |
| konc. | concentrated |
| Me | methyl |
| Min | minute(s) |
| MS | mass spectrum |
| NMR: | nuclear magnetic resonance |
| RF | reflux (heating at boiling temperature) |
| RT | room temperature |
| m.p. | melting point |
| T | temperature |
| TBME | tert butylmethylether |
| THF | tetrahydrofuran (dist. over Na) |

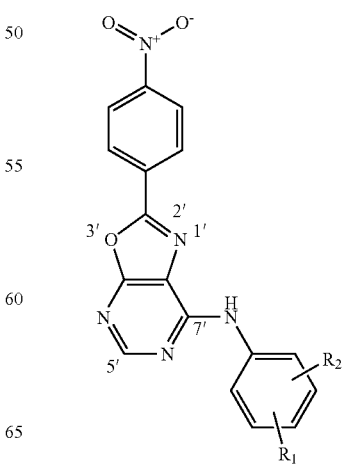

-continued

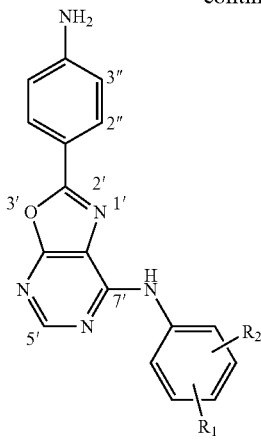

Example 1

3-{2'-(4"-aminophenyl)oxazolo[5,4-d]pyrimidin-7'-ylamino}phenol 0.574 g (1.64 mmols) of 3-{2'-(4"-nitrophenyl)oxazolo[5,4-d]pyrimidin-7'-ylamino}phenol are suspended together with 1.6 ml of catalyst suspension (ethanolic Raney nickel) in ca. 20 ml of THF, and shaken over night under $H_2$ at normal pressure. The solution is filtered by suction and the filtrate is mixed with ca. 50 ml $H_2O$, whereupon a light brown deposit forms, which is filtered off by suction. After a few days, a dark brown deposit forms in the filtrate. This is removed by suction. Again, a beige solid precipitates from the filtrate. This is separated and dried in a high vacuum. m.p.: ~285° C.; $^1$H4MR (300 MHz, DMSO): 9.96, 9.39 (s, NH, OH); 8.41 (s, HC(5')); 7.88 (dd, J=1.8, 8.7, H—C(3")); 7.47 (pseudo t, J2,2 H—C(2)); 7.30 (dd, J=8.1, 1.1, 1H); 7.12 (pseudo t, J=8.1, H—C(5)); 6.72 (dd, J=6.9, 1.8, H—C(2")); 6.48 (m, 1H); 6.08 (s, $NH_2$).

Example 1a

3-{2'-(4"-nitrophenyl)oxazolo[5,4-d]pyrimidin-7'-ylamino}phenol 452 mg (1.64 mmols) of 7-chloro-2-(4'-nitrophenyl)oxazolo[5,4-d]pyrimidine are suspended with 587 mg (5.38 mmols) of 3-aminophenol (Fluka, Buchs, Switzerland) in ca. 100 ml of n-butanol, and heated to RF for 90 minutes. After cooling to RT, a violet residue is filtered by suction. This is washed with a little n-butanol and dried in a HV. m.p.: >250° C.; Anal. calc. for $C_{17}H_{11}N_5O_4$ (349.31): C, 58.45; H, 3.17; N, 20.05, O 18.32; found: C 57.89, H 3.36, N 19.88, O 18.19.

The starting material is prepared as follows:

7-chloro-2-(4'-nitrophenyl)oxazolo[5,4-d]pyrimidine 6.83 g (41.8 mmols) of 5-amino4,6-dihydroxypyrimidine (prepared from 4,6-dihydroxy-5-nitropyrimidine (Aldrich, Switzerland) by reduction with tin(II) chloride according to M. Ishidate et al., Chem. Pharm. Bull. 8, 137-139 (1960)) are dissolved in ca. 100 ml of abs pyridine and mixed with 9.84 g (52.9 mmols) of 4-nitrobenzoyl chloride, heated to RF for ca. 1 h under an Ar atmosphere, and then concentrated by evaporation at 75° C. 75 ml of phosphorus oxychloride are added to the dark red residue and the reaction mixture is heated under RF for 1 h under an Ar atmosphere. After cooling, the reaction mixture is concentrated by evaporation (T<60° C.) and afterwards added to a NaOAc/Ice mixture with constant stirring. The suspension is set at pH 5 with NaOAc and filtered by suction. The residue is washed with $H_2O$ and EtOH. The residue which is dried in a HV is boiled in ca. 150 ml of EtOH, filtered by suction whilst warm and dried in a HV. A brown solid is obtained. Purification by column chromatography (silica gel, ethyl acetate/pentane 90:10-75:25) yields the title compound as colourless to pale yellow needles. m.p.: 231° C.

Example 2

7-(3"-chloroanilino)-2-(4'-aminophenyl)oxazolo[5,4-d]pyrimidine hydrochloride 1.61 g (4.4 mmols) of 7-(3"-chloroanilino)-2-(4'-nitrophenyl)oxazolo[5,4-d]pyrimidine ar suspended in a water bath at RT in ca. 10 ml of conc. hydrochloric acid and 10 ml of ethanol. After adding 2.50 g of $SnCl_2$, the water bath is heated to ca. 80° C. After ca. 100 min, 40 ml of conc. hydrochloric acid are added and the water bath is removed. The suspension cooled to RT is filtered by suction and the residue dried in a HV. The residue is suspended again in $H_2O$, left to stand, filtered by suction and the residue dried in a HV. m.p.: 260-270° C. partial decomposition). $^1$H-NMR (300 MHz, DMSO): 10.36, (s, NH); 8.50 (s, H—C(5)); 8.16 (m, H—C(2")); 7.95 (d, J=8.7, H—C(2')); 7.85 (dd, J=2, 0.9, 1H); 7.34 (pseudo t, J=8.1, H—C(5")); 7.12 (ddd, J=6.3, 2, 0.9, 1H); 6.9 (d, J=8.8, H—C(3')).

Example 2a

7-(3"-chloroanilino)-2-(4'-nitrophenyl)oxazolo[5,4-d]pyrimidine 150 mg (0.54 mmols) of 7-chloro-2-(4'-nitrophenyl)oxazolo[5,4-d]pyrimidine are suspended together with 0.17 ml (1.6 mmols) of 3-chloroaniline (Fluka, Buchs, Switzerland) in ca. 30 ml of n-butanol, and heated to RF for ca. 2 h. After removing the heating bath, a solid precipitates. The solid is filtered by suction, washed with a little n-butanol and dried in a HV. m.p.: 282-287° C. Anal. calc. for $C_{17}H_{10}ClN_5O_3$ (376.76): C, 55.52; H, 2.74; N, 19.04, O, 13.05; found C, 55.15H 3.04, N, 18.59, O, 13.98.

Example 3

4-{2'-(4"-aminophenyl)oxazolo[5,4-d]pyrimidin-7'-ylamino}phenol 350 mg (1.0 mmols) of 4-{2'-(4"-nitrophenyl)oxazolo[5,4-d]pyrimidin-7'-ylamino}are suspended in 100 ml of THF and 20 ml of DMEU, mixed with a spatula tip of Raney nickel catalyst (ethanolic suspension), and shaken over the weekend under $H_2$ at normal pressure. The resulting suspension is filtered by suction, the filtrate concentrated and mixed with ca. 150 ml of $H_2O$. Again, the suspension obtained is filtered by suction, the residue washed with $H_2O$ and dried in a HV. The crude product is again dissolved in warm THF and immediately filtered by suction. This filtrate is concentrated by evaporation and the reddish residue is dried in a HV at 150° C. m.p.: >250° C. IR: 3446w, 3311 w, 3194w, 1618s, 1509s, 1483s, 1439m, 1322m, 1312m, 1267m, 1225m, 1171w, 1080w.

Example 3a

4-{2'-(4'-nitrophenyl)oxazolo[5,4d]Pyrimidin-7'-ylamino}phenol 2.22 g (8.0 mmols) of 7-chloro-2-(4'-nitrophenyl)oxazolo[5,4-d]pyrimidine are heated to reflux for 3 h with 2.58 g (23.6 mmols) of 4-aminophenol (Fluka, Buchs, Switzerland) in 350 ml of n-butanol. The orange-red suspension is allowed to cool to RT. Afterwards, it is filtered by suction, and the residue is dried in a HV (m.p. >300° C.), then suspended in ca. 40 ml of 98% EtOH (ca. 70° C.), filtered by suction again and dried in a HV [crystalline, m.p. >300° C.]. IR: 3360w, 3178w, 1630m, 1607m, 1518m, 1482w, 1348m, 1217m, 1079w, 1045w, 855w, 710w, 516w.

Example 4

7-(4"-chloroanilino)2-(4'-aminophenyl)oxazolo[5,4-d]pyrimidine 0.536 g (2.93 mmols) of 7-(4"-chloroanilino)-2-(4'-nitrophenyl)oxazolo[5,4-d]pyrimidine are suspended with a spatula tip of Raney nickel catalyst (ethanolic suspension) in ca. 15 ml of DMEU and ca. 75 ml of THF, and shaken for 22 h under $H_2$ at normal pressure, and then filtered by suction. The residue is concentrated and mixed with $H_2O$. The suspension thus obtained is filtered by suction again, dried in a HV, dissolved in THF and mixed with MeOH. The suspension thus obtained is filtered by suction. The residue is dried in a HV; m.p.: 296-301° C.

Example 4a 7-(4"-hloroanilino)-2-(4'-nitrophenyl)oxazolo[5,4-d]pyrimidine 1.99 g (7.2 mmols) of 7-chloro-2-(4-nitrophenyl)oxazolo[5,4-d]pyrimidine are heated to RF for 90 min with 2.75 g (21.6 mmols) of 4-chloroaniline (Fluka, Switzerland) in ca. 300 ml of n-butanol. After cooling to RT, the suspension is filtered by suction and the residue is washed with a little methanol and a lot of EtOH, dried in a HV, then heated in ca. 400 ml of DMSO and filtered whilst hot. Flakes precipitate from the filtrate; m.p.: ca. 300° C. $^1$H-NMR (300 MHz, DMSO): 10.6 (s, NH); 8.57 (s, H—C(5)); 8.49 (d, J=8.9, 2H); 8.43 (d, J=9.0, 2H); 7.98 (d, J=9.0, H—C(2")); 7.44 (d, J=8.8, H—C(3")).

Further examples: The following compounds of formula A are produced analogously to the above-mentioned examples and methods, using 7-chloro-2-(3'-nitrophenyl)oxazolo[5,4-d]pyrimidine (for preparation see footnote[10]) instead of 7-chloro-2-(4'-nitrophenyl)oxazolo[5,4-d]pyrimidine. From the compounds of formulal A, compounds of formula B are obtained by reduction:

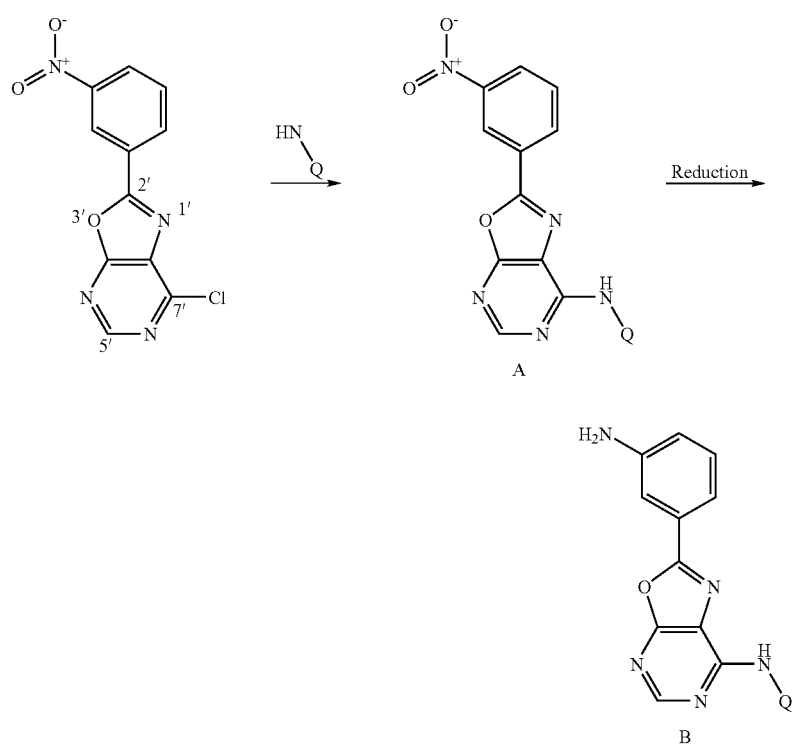

| Ex. | structure type | preparation analog. to Ex. | QNH— | educt | m.p. [° C.] |
|---|---|---|---|---|---|

-continued

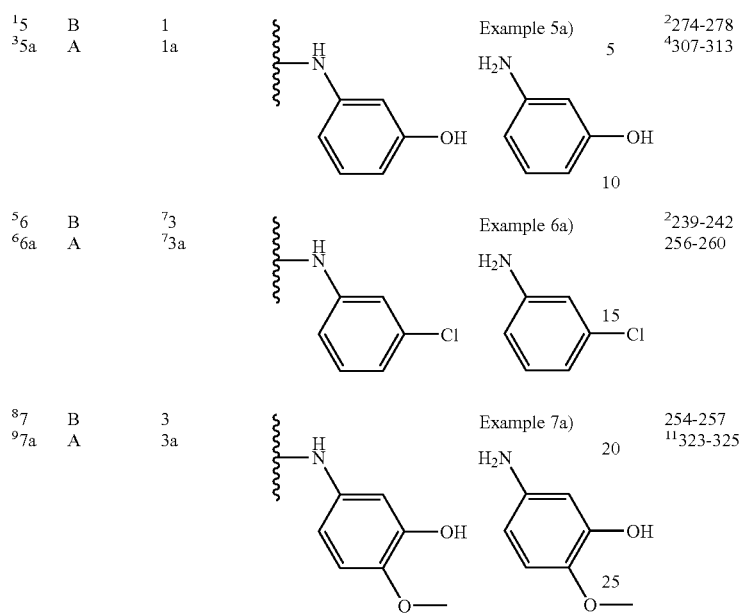

| [1]5  | B | 1  | Example 5a) | [2]274-278 |
| [3]5a | A | 1a |             | [4]307-313 |
| [5]6  | B | [7]3  | Example 6a) | [2]239-242 |
| [6]6a | A | [7]3a |             | 256-260 |
| [8]7  | B | 3  | Example 7a) | 254-257 |
| [9]7a | A | 3a |             | [11]323-325 |

$^1$H-NMR signals (300 MHz, DMSO-$d_6$)

Example 5: 10.18, 9.44 (s, NH, OH); 8.49 (s, —H—C(5'); 7.47 (pseudo t, J = 2.1, 1H); 7.41 (pseudo t, J = 1.9, 1H); 7.39-7.11 (m, 3H); 7.14 (pseudo t, J = 8.1, H—C(5); 6.83 (ddd, J = 8.0, 2.3, 1.0, 1H); 6.52 (ddd, J = 8.1, 2.4, 0.9, H—C(6)); 5.55 (s, $NH_2$).

Example 5a: 10.32, 9.45 (s, NH, OH); 8.98 (pseudo t, J = 2.0, H—C(2")); 8.58 (pseudo d, J = 7.3, 1H); 8.55 (s, H—C(5')); 8.50 (d x pseudo t, J = 8.4, 1.2, 1H); 7.97 *pseudo t, J = 8.0, H—C(5")); 7.49 (pseudo t, J = 2.0, H—C(2)); 7.34 (d x pseudo d, J = 8.0, 1.2, H—C(4)); 7.16 (pseudo t, J = 8.1, H—C(5)); 6.55 (d x pseudo d, J = 7.6, 2.1, H—C(6)).

Example 6: 10.51 (s, NH); 8.56 (s, H—C(5)); 8.71 (pseudo t, J = 2.0, H—C(2')); 7.88 (ddd, J = 8.3, 2.1, 0.9, 1H); 7.43-7.36 (m, 3H); 7.28 (pseudo t, J = 7.8, H—C(5')); 7.15 (ddd, J = 8.0, 2.1, 0.9, 1H); 6.84 (ddd, J = 8.0, 2.3, 1.1, 1H); 5.56 (s, $NH_2$).

Example 6a: 10.60 (s, NH); 8.96 (pseudo t, J = 1.9, H—C(2')); 8.62 (s, H—C(5)); 8.58 (pseudo d, J = 7.7, 1H); 8.49 (ddd, J = 8.3, 2.3, 0.9, 1H); 8.18 (pseudo t, J = 2.0, H—C(2")); 7.96 (pseudo t, J = 8.0, H—C(5')); 7.88 (pseudo d, J = 7.7, H—C(6")); 7.41 (pseudo t, J = 8.1, H—C(5")); 7.17 (pseudo d, J = 8.2, H—C(4")).

Example 7: 10.02, 9.04 (s, NH, OH); 8.42 (s, H—C(5')); 7.40-7.34 (m, 3H); 7.29-7.20 (m, 2H); 6.91 (d, J = 8.8, 1H); 6.83 (dd, J = 8.0, 1.0, 1H); 5.53 (s, $NH_2$); 3.78 (s, $CH_3O$).

Example 7a: 10.19, 9.07 (s, NH, OH); 8.95 (pseudo t, J = 1.8, H—C(2")); 8.57 (pseudo d, J = 7.8, 1H); 8.51-8.47 (m, 2H); 7.96 (t, J = 8.1, H—C(5")); 7.24 (d, J = 2.6, H—C(6)); 7.24 (dd, J = 8.8, 2.6, H—C(4)); 6.93 (d, J = 8.8, H—C(3)); 3.79(s, $H_3C$).

[1]Name: 3-{2'-(3"-aminophenyl)oxazolo[5,4-d]pyrimidin-7'-ylamino}phenol; additional purification step at the end: column chromatography after absorption on 10 g of silica gel applied as a powder, and eluted with $CH_2Cl_2$:Methanol 100:0-95:5.

[2]with partial decomposition.

[3]Name: 3-{2'-(3"-nitrophenyl)oxazolo[5,4-d]pyrimidin-7'-ylamino}phenol;

[4]at around 290° C., forms platelets which then melt at around 307-313° C.

[5]Name: 7-(3"-chloroanilino)-2-(3'-aminophenyl)oxazolo[5,4-d]pyrimidine:

[6]Name: 7-(3"-chloroanilino)-2-(3'-nitrophenyl)oxazolo[5,4-d]pyrimidine:

[7]additional purification step at the end: column chromatography on silica gel, $CH_2Cl_2$:methanol 99:1-96:4.

[8]Name: 2-methoxy-5-{2'-(3"-aminophenyl)oxazolo[5,4-d]pyrimidin-7'-ylamino}phenol.

[9]Name: 2-methoxy-5-{2'-(3"-nitrophenyl)oxazolo[5,4-d]pyrimidin-7'-ylamino}phenol.

[10]preparation of 7-chloro-2-(3'-nitrophenyl)oxazolo[5,4-d]pyrimidine: 2.25 g (17.7 mmols) of 5-amino-4,6-dihydroxypyrimidine (for preparation see example 1 b)) are suspended in ca. 100 ml of absolute pyridine together with 3.73 g (20.0 mmols) of 3-nitrobenzoyl chloride (Fluka, Buchs, Switzerland), heated under RF for 1 h under an Ar atmosphere, then concentrated by evaporation at 7° C. and dried in a HV. The residue is heated to RF for close to 2 h in ca. 100 ml of phosphorus oxychloride under an Ar atmosphere, concentrated by evaporation (T < 60° C.), and then added to a NaOAc/ice mixture whilst stirring constantly. The suspension is set at pH 5 with NaOAc, left to stand over night and filtered by suction the next day. The residue is washed with $H_2O$, boiled out in a lot of ethanol, and filtered whilst hot. The filtrate is left for one week in a refrigerator, filtered by suction and the residue dried in a HV. Working up by column chromatography (ethyl acetate/pentane 1:0-2:1) yields the title compound: m.p. 144-147° C.

[11]at around 260° C., forms crystals which then melt at around 323-325° C.

Example 8

4-(4-chloro-2-fluoroanilino)-6-(4-aminophenyl)furo[2,3-d]pyrimidine 0.95 g (2.5 mmols) of 4-(4-chloro-2-fluoranilino)-6-(4-nitrophenyl)furo[2,3-d]pyrimidine suspended in ca. 50 ml of THF, 2 ml of triethylamine and 2 ml of DMEU, mixed with a spatula tip of catalyst suspension (ethanolic Raney nickel) and shaken over night under $H_2$ at normal pressure. The suspension is filtered by suction through Celite, concentrated by evaporation, mixed with $H_2O$, set at pH 10 with 5% NaOH solution, filtered by suction, and the residue washed with a lot of $H_2O$. The product is worked up by column chromatography (dissolved in acetone and added to the column as a silica gel adsorbate, silica gel, pentane:ethyl acetate=3:2, m.p.: 229-232° C.

Example 8a

4-(4-chloro-2-fluoroanilino)-6-(4-nitrophenyl)furo[2,3-d]pyrimidine 1.65 g (5.9 mmols) of 4-chloro-6-(4-nitrophenyl)furo[2,3-d]pyrimidine are heated for ca. 4 h until boiling with 2.2 ml of 4-chloro-2-fluoroaniline in 100 ml of 1-butanol. The mixture is allowed to cool and filtered by suction. The residue is washed, in succession, with a lot of 1-butanol, methanol and tert.-butylmethylether, and dried in a HV. The crude product is recrystallised from acetic acid. m.p.: >250° C., $^1$H-NMR (500 MHz, DMSO)†: 10.0 (s, NH); 8.41 (s, H—C(2)); 8.36 (d, J=9.1, H—C(2')); 8.08 (d, J=9.0, H—C(3')); 7.82 (pseudo t, J=8.6, H—C(6")); 7.78 (s, H—C(5)); 7.57 (dd, J=10.4, 2.4, H—C(3")); 7.35 (ddd, J=8.6, 2.4, 1.1, H—C(5")).

†classification based on HETCOR and long range HERCOR experiments.

The starting material is prepared as follows:

8a1: 4-chloro-6-(4-nitrophenyl)furo[2,3-d]pyrimidine:

13.5 g of 4-hydroxy-6-(4-nitrophenyl)furo[2,3-d]pyrimidine are heated for 1.5 h under RF in ca. 200 ml of phosphorus oxychloride (Fluka, Buchs). Afterwards, the reaction mixture is left to stand in the open for 3 days, and then added to 4 kg of ice. The suspension is filtered by suction and washed with a lot of $H_2O$. The product is sublimated at ca. 200° C. and at ca. 0.1 mbar. The sublimate consists of lemon-yellow non-crystalline needles: m.p.: from 245° C. (decomposition). $^1$H-NMR (300 MHz, DMSO): 8.91 (s, H—C(2)); 8.40, 8.31 (d, J=9.2, H—C(2', 3')); 8.09 (s, H—C(5)).

8a2: 4-hydroxy-6-(4-nitrophenyl)furo[2,3-d]pyrimidine:

21 g of 4-hydroxy-6-(4-nitrophenyl)furo[2,3-d]pyrimidine-5-carboxylic acid are dissolved in ca. 200 ml of pyridine whilst heating, and subsequently concentrated by evaporation at 80° C. The residue is heated to 190° C. for 1 h, with a constant stream of nitrogen, in 500 ml of quinoline, which has been dried over magnesium sulfate, with 1 g of $Cu_2O$ (Aldrich, Buchs). The reaction mixture is allowed to cool and is added to 1 litre of 2.5 M hydrochloric acid, stirred and filtered by suction. The residue is washed with conc. ammonia solution and with $H_2O$. The dark brown residue is dried in a HV: m.p.: >350° C.

8a3: 4-hydroxy-6-(4-nitronhenyl)furo[2,3-d]pyrimidine-5-carboxylic acid 3.0 g (9.1 mmols) of 4-hydroxy-6-(4-nitrophenyl)furo[2,3-d]pyrimidine-5-carboxylic acid ethyl ester are boiled for 50 min in ca. 50 ml of 5% sodium hydroxide solution. The reaction mixture is suction-filtered whilst hot and the residue discarded. [In order to obtain the sodium 4-hydroxy-6-(4-nitrophenyl)furo[2,3-d]pyrimidine-5-carboxylate, the cold filtrate (after cooling, needles form) is filtered by suction over ice and washed with a little ice water. The needles are dried in a HV. M.p. >250° C. (decomposition).] After cooling, the filtrate is carefully adjusted to pH 1 with conc. hydrochloric acid (a precipitate forms). Filtering by suction and drying of the residue in a HV yield the title compound as a solid, which melts at 300-302° C. (decomposition at the melting point):

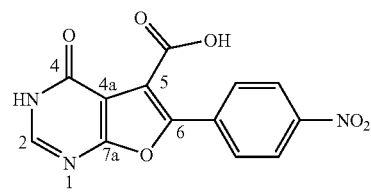

m.p.: >300° C. (melting/decomposition).
$^1$H-NMR (300 MHz, DMSO): 13.5 (bs, COOH); 8.40 (s, C(2)-H); 8.38 (d, J = 7.0, arH); 8.17 (d, J = 9.1, arH).

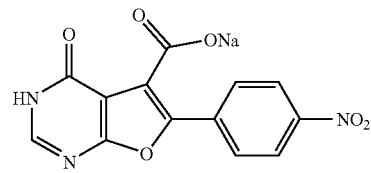

m.p.: >350° C. $^1$H-NMR (300 MHz, $D_2O$, details relating to HDO = 4.79 ppm); 8.24 (d, J = 9.2, arH, 2H); 8.08 (s, arH, 1H); 7.93 (d, J = 9.2, arH, 2H).

8a4: 4-hydroxy-6-(4-nitronhenyl)furo[2,3-d]pyrimidine-5-carboxylic acid ethyl ester 7.34 g of 2-amino-5-(4-nitrophenyl)furan-3,4-dicarboxylic acid diethyl ester are stirred for 14 h at 140° C. under $N_2$ in 40 ml of formamide, 20 ml of DMF and 10 ml of 98-100% formic acid. The reaction mixture is cooled by an ice bath. Afterwards, a viscous mass is filtered off and washed first of all with propan-2-ol and then with hexane. The residue is dried in a HV, heated in 200 ml of EtOH and suction-filtered whilst hot. Drying of the residue in a HV yields the title compound: m.p.: 279-282° C.

8a5: 2-amino-5-(4-nitrophenyl)furan-3,4-dicarboxylic acid diethylester 105 g (0.39 mols, 1 eq) of 4-nitrobenzoyl-chloroacetic acid ethyl ester are dissolved in 600 ml of THF. To this solution are added, on a water bath (T=35° C.), in portions, 49.4 g (0.37 mols) of finely ground sodium cyanoacetic acid ethyl ester (preparation: Chem, Ber. 1962, 95, 307-318.). It is stirred over night (under $N_2$), fully concentrated by evaporation, and extracted with $H_2O$ and $CH_2Cl_2$. The combined $CH_2Cl_2$ phase is washed with $H_2O$, and finally dried over $MgSO_4$ and freed from solvent. Crystallisation from toluene yields the title compound, m.p.: 174-177° C.

8a6: 4-nitrobenzoyl-chloroacetic acid ethylester (2-chloro-3-(4-nitrophenyl)-3-oxo-propanoic acid ethylester)

Described in *J. Heterocycl. Chem.* 1985, 32, 1621-1630 (and references therein). Simplified preparation: 100.2 g (0.42 mols) of 4-nitrobenzoyl-acetic acid ethylester (Acros, Belgium) are suspended in 350 ml of toluene and mixed with 45 ml (75 g; 0.55 mols) of $SO_2Cl_2$. Stirring is effected for 1 h at 80° C. under reduced pressure (ca. 900 hPa). Subsequently, the temperature and the pressure are gradually reduced. The residue is quenched with ice water and extracted several times with toluene. The organic phase is washed with $H_2O$ and finally neutralised with sat. $NaHCO_3$ solution, dried ($MgSO_4$) and concentrated to form the title compound.

The following derivatives are prepared in the manner analogous to that described in Example 8:

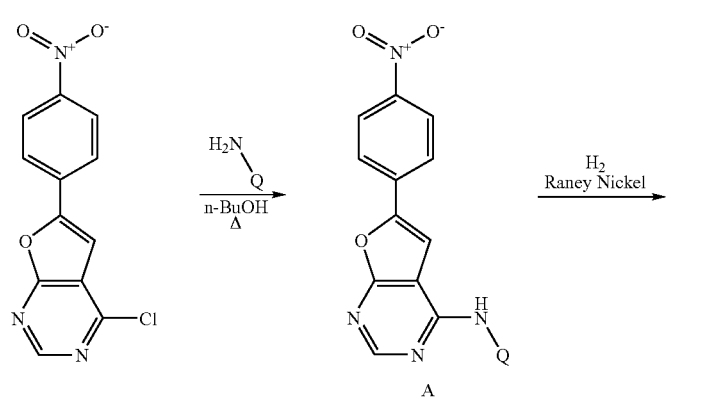

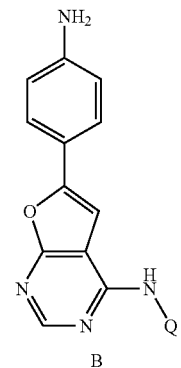

| Ex | structure type | HN-Q | EI-MS M+ | elementary analysis[1] | m.p. [° C.] |
|---|---|---|---|---|---|
| 9 | B | HN- | 336 | CHNO[2] | 254 |
| 9a | A | HN-(3-Cl-phenyl) | 366 | CHNO | 288 |
| 10 | B | HN-(4-hydroxy-3-methoxyphenyl) | 348 | CHNO | 261-263 |
| 10a | A |  | 378 |  |  |

-continued

| | | | | | |
|---|---|---|---|---|---|
| 11 | B | 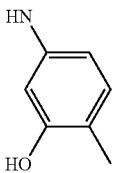 | 332 | CHNO | 295 |
| 11a | A | | 362 | CHNO | |
| 12 | B | 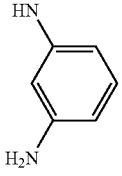 | 317 | | 225-230 |
| 12a | A | 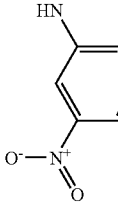 | 377 | CHNO | >350 |

[1] Difference between calculated and measured value ≦0.4%
[2] $C_{calc}$: 64.20%; $C_{found}$: 63.78%

Example 13

4-(1R-phenylethylamino)-6-(3-aminophenyl)furo[2,3-d]pyrimidine 1.47 g (4.1 mmols) of 4-(1R-phenylethylamino)-6-(3-nitrophenyl)furo[2,3-]pyrimidine are dissolved in ca. 50 ml of THF, mixed with a spatula tip of Raney nickel suspension, shaken over night under $H_2$ at normal pressure, filtered by suction through Celite, the filtrate concentrated by evaporation, taken up in TBME and extracted $H_2O$. The organic phase is dried over $MgSO_4$, concentrated by evaporation and dried in a HV. The product is taken up in $CH_2Cl_2$, extracted with semi-concentrated hydrochloric acid, the aqueous phase is separated, neutralised with sat. $NaHCO_3$ solution and back-extracted with $CH_2Cl_2$. Drying of the organic phase over $MgSO_4$ and concentrating by evaporation yield the title compound. M.p.: 64-84° C. IR: 3340m br, 3028w, 2972w, 1600s, 1570m, 1491 m, 1466 m, 1352m, 1303m, 1228w, 1141 m, 941 w, 776m, 700m, 551 w. EI-MS: 330 (M+).

The starting material is prepared as follows:

13a: 4-(1R-phenylethylamino)-6-(3-nitrophenyl)furo[2,3-d]pyrimidine 2.43 g (8.8 mmols) of 4-chloro-6-(3-nitrophenyl)furo[2,3-d]pyrimidine are heated for 2.5 h until boiling with 4.2 ml of R—(+)-α-methylbenzylamino (Fluka, Buchs, [3886-69-9]) in ca. 75 ml of 1-butanol. The solution is concentrated by evaporation (80° C., 100 mbar), mixed with 100 ml of $H_2O$ and 300 ml of TBME and shaken, whereupon a precipitate forms. The two-phase mixture is filtered by suction and the residue dried in a HV. Recrystallisation from EtOH yields the title compound, m.p. 163-165° C.

The starting material is prepared as follows:

13b: 4-chloro-6-(3-nitrophenyl)furo[2,3-d]pyrimidine 11 g of 4-hydroxy-6-(3-nitrophenyl)furo[2,3-d]pyrimidine are heated for 4 h to RF in ca. 340 ml of phosphorus oxychloride. Afterwards, the reaction mixture is left to stand over night and then added to 5 kg of drained ice. The resulting suspension is filtered by suction and washed with a lot of $H_2O$. The residue is dried in a HV and sublimated at ca. 200° C.; m.p.: 196-205° C.

The starting material is prepared as follows:

13c: 4-hydroxy-6-(3-nitrophenyl)furo[2,3-d]pyrimidine 18.4 g of 4-hydroxy-6-(3-nitrophenyl)furo[2,3-d]pyrimidine-5-carboxylic acid are placed in ca. 200 ml of quinoline, and heated for 20 min to 200-220° C. under a constant stream of $N_2$. Then, 0.7 g of $Cu_2O$ are added. After 2 hours, an additional 0.4 g of $Cu_2O$ is added. 1 hour later, another spatula tip of $Cu_2O$ is added and the temperature lowered. The next day, the reaction mixture is mixed with 0.5 litres of 2.5 M HCl, diluted with $H_2O$, stirred, left to stand for 8 h and filtered by suction. The residue is washed with conc. ammonia and with a lot of $H_2O$. The basic filtrate is acidified with conc. HCl, filtered by suction and washed with a lot of $H_2O$. The crude product from the two residues is used directly without further working up m.p.: >300° C. IR: 3091 w, 2853w, 1670ss, 1593w, 1527s, 1496w, 1475w, 1373w, 1348s, 1297w, 1202m, 938m, 900m, 783w, 740w, 703w, 622w.

The starting material is prepared as follows:

13d: 4-hydroxy-6-(3-nitrophenyl)furo[2,3-d]pyrimidine-5-carboxylic acid 0.95 g (3.2 mmols) of 4-hydroxy-6-(3-nitrophenyl)furo[2,3-d]pyrimidine-5-carboxylic acid ethyl ester are place in 30 ml of 5% sodium hydroxide solution and heated for 30 min to 100° C. The reaction mixture is filtered whilst hot and the filtrate cooled to RT. Subsequently, the pH value of the solution is adjusted to 1 with conc. hydrochloric acid, whilst cooling. A brown deposit forms, which is filtered off by suction and dried in a HV. m.p.: >300° C. IR: 3448w, 3237m, 3088w, 1752s, 1734s, 1672s, 1531s, 1474m, 1407m, 1381m, 1346s, 1241m, 1211m.

The starting material is prepared as follows:

13e: 4-hydroxy-6-(3-nitrophenyl)furo[2,3-d]pyrimidine-5-carboxylic acid ethyl ester 72.9 g of 2-amino-5-(3-nitrophenyl)furan-3,4-dicarboxylic acid diethyl ester are stirred for ca. 23 h at 140° C. under $N_2$ in 200 ml of formamide, 100 ml of DMF and 40 ml of 98-100% formic acid. After cooling the solution, the reaction mixture is diluted with $H_2O$, left to stand for 8 h and filtered by suction. The residue is dried in a HV, boiled in 300 ml of acetonitrile, filtered by suction, washed with ice-cold acetonitrile and dried in a HV. This second residue is boiled in 200 ml of methylene chloride, filtered by suction whilst warm, washed with methylene chloride and dried in a HV. The residue obtained contains the product; m.p.: 212-220° C. IR: 3528w, 3246m, 3092m, 2985w, 1936w, 1721s, 1589s, 1543s, 1482m, 1429w, 1378s, 1352s, 1323m, 1287m, 1234m, 1196m, 1076m, 1042s. In the product thus obtained, 4-hydroxy-6-(3-nitrophenyl)furo[2,3-d]pyrimidin-5-carboxylic acid amide is obtained as a by-product. This is obtained in analysis-pure form by recrystallisation from DMF; m.p.: ca. 380° C. (decomposition) IR: 3338m, 3180-2810w (multiplett), 1708s, 1676s, 1589w, 1560m, 1526s, 1406w, 1348s, 1220w, 1105w, 1081w, 1041w, 920w, 899w, 880w, 803w, 740w, 676w.

The starting material is prepared as follows:

13f: 2-amino-5-(3-nitrophenylfuran-3,4-dicarboxlic acid diethylester 25 g of (3-nitrophenyl)-3-oxopropanoic acid ethylester (0.10 mols; Acros, Belgium) are placed in 300 ml of toluene. 12.8 ml of sulfuryl chloride (0.15 mols) are added to this suspension at RT. After a further 10 min, the reaction is quenched with 150 ml of $H_2O$. The organic phase is extracted with sat. sodium hydrogen carbonate solution until the aqueous phase has a pH of >7. Afterwards, the organic phase is extracted again with $H_2O$, dried with magnesium sulfate and filtered by suction. The toluene is evaporated. 180 g of the oil obtained is placed in 400 ml of THF distilled over Na and under Ar. 79.6 g of finely powdered sodium cyanoacetic ester (0.59 mols) are added in portions to this solution whilst cooling (preparation: *Chem. Ber.* 1962, 95, 307-318.). After stirring for 3 h at 25° C., the THF is removed, the oily residue taken up with $CH_2Cl_2$ and extracted with $H_2O$. The organic phase is dried with magnesium sulfate, filtered by suction and the solvent evaporated. An orange-coloured oil is obtained, which is crystallised from p-xylene. m.p.: 169° C.

The following derivatives are also produced from A (ex. 13a) analogously to example 8.

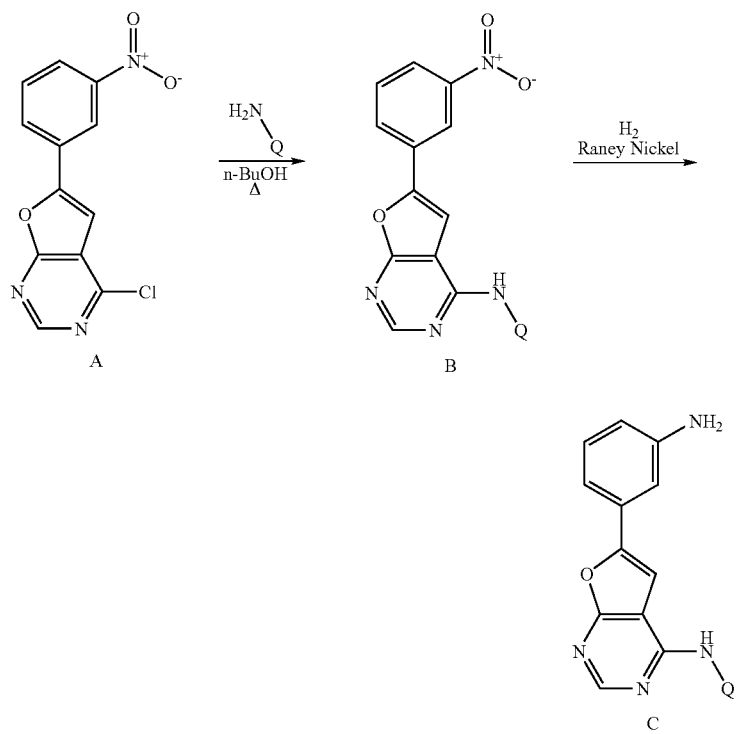

-continued
| Ex. | structure type | HN—Q | EI-MS M+ | elementary analysis[1] | m.p. [° C.] |
|---|---|---|---|---|---|
| 14 | C | 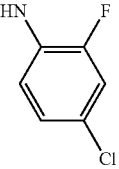 | 354 | CHNO | 216 |
| 14a | B | | 384 | CHNO | 269 |
| 15 | C | 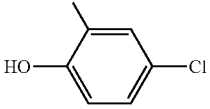 | 352 | | ≈240 |
| 15a | B | | 382 | | ≈275 |
| 16 | C | 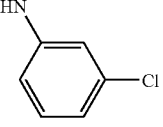 | | CHNO | 244-245 |
| 16a | B | | 366 | CHNO | 268-270 |
| 17 | C | 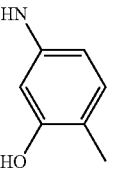 | 332 | | 233-234 |
| 17a | B | | 362 | | 280-285 |
| 18 | C | 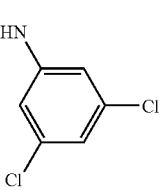 | 370 | | 135-137 |
| 18a | B | | 400 | | |
[1]Difference between calculated and measured value ≦0.4%

The following derivatives can be produced analogously to the above examples:
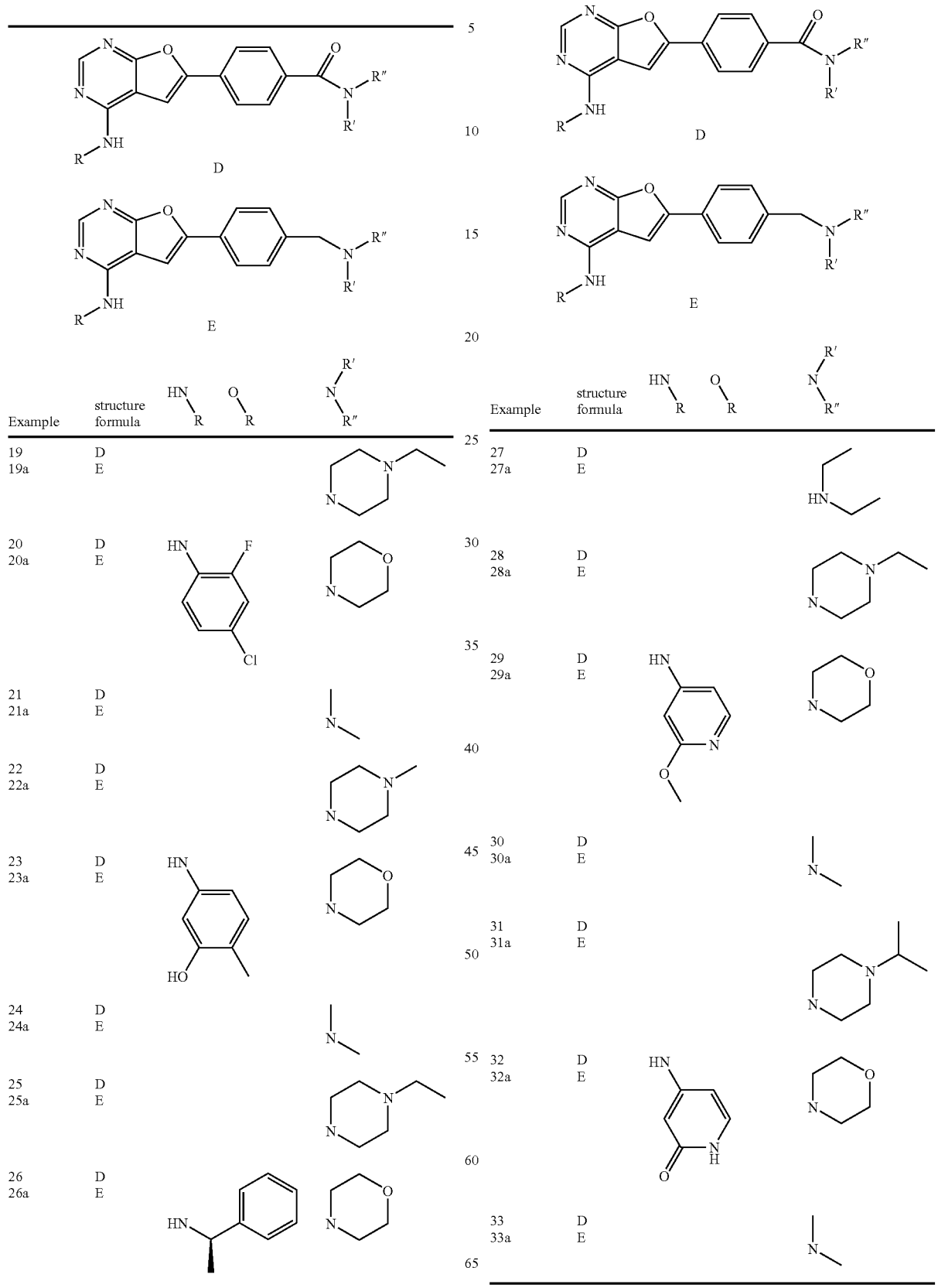

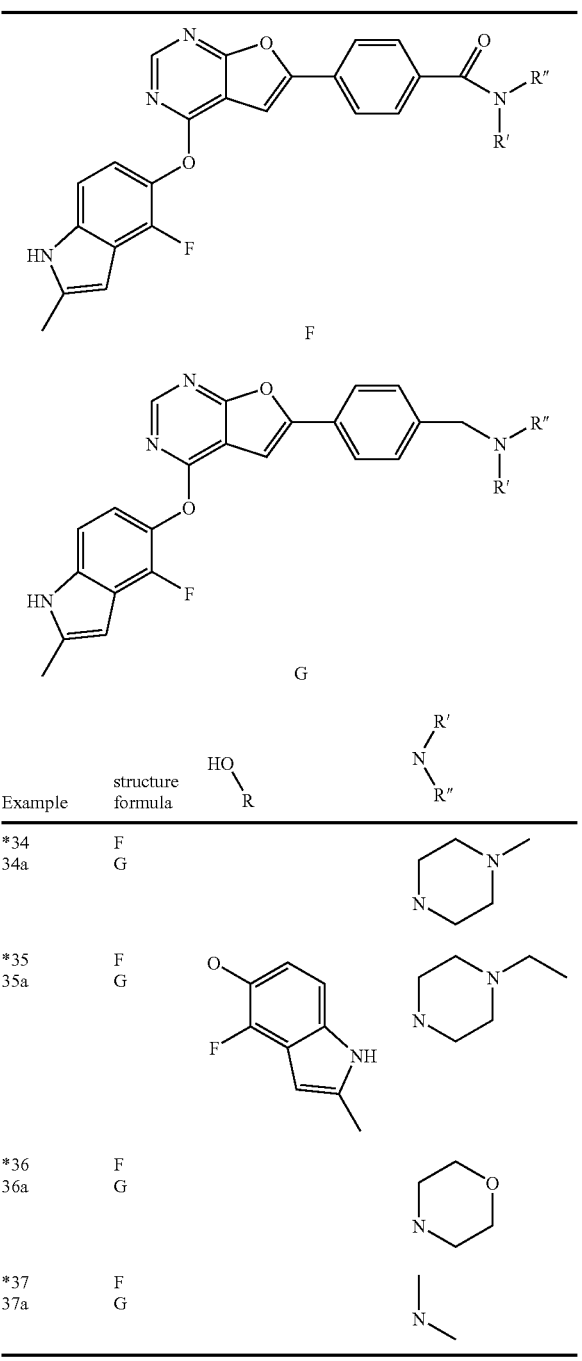

| Example | structure formula | R | N(R')(R'') |
|---|---|---|---|
| *34 | F | | piperazine-N-methyl |
| 34a | G | | |
| *35 | F | | piperazine-N-ethyl |
| 35a | G | | |
| *36 | F | | morpholine |
| 36a | G | | |
| *37 | F | | N(CH3)2 |
| 37a | G | | |

*synthesis of 4-fluoro-2-methyl-1.H.-indol-5-ol described in WO 00/47212, example 237.

The starting material is prepared as follows:

a) 4-benzyloxycarbonylacetyl-benzoic acid methylester

Under an $N_2$ atmosphere, 9.5 g of $MgCl_2$ (100 mmols, dried at 130° C. in a HV) are suspended in 100 ml of $CH_2Cl_2$ and mixed, whilst cooling with ice, with 25.0 g of benzyl-tert.-butylmalonate (100 mmols) and 27.9 ml of triethylamine (200 mmols). After 15 min, 19.8 g of 4-chlorocarbonyl-benzoic acid methylester (100 mmols) dissolved in 30 ml of $CH_2Cl_2$ are added over the course of 30 minutes, and stirred over night at RT. The reaction mixture is mixed with ice water, the aqueous phase separated and extracted with $CH_2Cl_2$. The organic phase is washed twice with 5% citric acid solution and brine, dried ($Na_2SO_4$), and concentrated by evaporation (50 g of an oil). The residue is dissolved in 400 ml of formic acid and stirred for 2 days at RT. The formic acid is evaporated under a vacuum. The residue of evaporation is dissolved in EtOAc and dilute $NaHCO_3$ solution, the aqueous phase separated and extracted twice more with EtOAc. The organic phases are washed with $NaHCO_3$ solution, $H_2O$ and brine, dried ($Na_2SO_4$) and concentrated by evaporation. The residue is dissolved in boiling toluene, partially concentrated and cooled down to RT. A formed precipitation is filtered off and discarded. The title compound was finally obtained from the filtrate by shortly cooling it in dry ice, filtration of the formed crystals and washing with cold toluene: m.p.: 71° C.

b) 4-(benzyloxycarbonyl-chloro-acetyl)-benzoic acid methylester 4.0 g (12.8 mmols) of 4-benzyloxycarbonylacetyl-benzoic acid methylester, dissolved in 40 ml of toluene, are mixed with 19.2 ml of a 1 M solution of $SO_2Cl_2$ in $CH_2Cl_2$ and stirred for 30 min at RT. At 0° C., water is added and the aqueous phase is separated and extracted twice with EtOAc. The organic phases are washed twice with sat. $NaHCO_3$ solution, $H_2O$ and brine, dried ($Na_2SO_4$) and concentrated by evaporation. Column chromatography ($SiO_2$; hexane/EtOAc 9:1→4:1; crude product dissolved in $CH_2Cl_2$) yielded the title compound as an oil: MS: $[M+1]^+=347$; TLC(hexane/EtOAc 4:1) Rf=0.19.

c) 2-amino-5-(4-methoxycarbonyl-phenyl)-furan-3.4-dicarboxylic acid-3-methyl-4-benzyl-ester Under $N_2$ atmosphere, 785 mg (2.28 mmols) of 4-(benzyloxycarbonyl-chloro-acetyl)-benzoic acid methylester, dissolved in 3.5 ml of THF, is stirred at 35° C. 284 mg (2.35 mmols) of finely powdered sodium cyanoacetic acid methyl ester (preparation: Chem. Ber. 1962, 95, 307-318) are added to this in portions. After 5 h, the mixture is filtrated, the filtrate concentrated by evaporation and the residue is taken up in $H_2O$ and EtOAc. The aqueous phase is separated and extracted twice with EtOAc. The organic phases are washed with $H_2O$ and brine, dried ($Na_2SO_4$) and concentrated by evaporation. Column chromatography ($SiO_2$; $CH_2Cl_2$→$CH_2Cl_2$/acetone 39:1) and crystallization from boiling toluene yields the title compound: m.p.: 138-139° C.; $^1$H-NMR ($CDCl_3$): 7.92 (d, 2H), 7.50 (d, 2H), 7.42 (m, 2H), 7.37 (m, 3H), 5.70 (s, $H_2N$), 5.38 (s, 2H), 3.91 (s, $H_3C$), 3.64 (s, $H_3C$).

d) 6-(4-methoxycarbonyl-phenyl)-4-oxo-3,4-dihydro-furo[2,3-d]pyrimidine-5-carboxylic acid benzylester Under a $N_2$ atmosphere, 100 mg (0.25 mmols) of 2-amino-5-(4-methoxycarbonyl-phenyl)-furan-3,4-dicarboxylic acid-3-methyl-4-benzyl-ester are dissolved in 1.25 ml of a mixture of $HCONH_2$, DMF and HCOOH (4:2:1) and stirred for 139 h at 120° C. The DMF is evaporated in vacuo. Recrystallization from boiling methanol gives the title compound: m.p.: 248-249° C.; MS: $[M+1]^+=405$; $^1$H-NMR (DMSO-$d_6$): 12.9 (s, 1H), 8.26 (s, 1H), 7.98 (d, 2H), 7.47 (m, 21), 7.35 (m, 3H), 5.38 (s, 2H), 3.88 (s, $H_3C$). Among other impurities, the filtrate contains 6-(4-methoxycarbonylphenyl)-4-oxo-3,4-dihydro-furo[2,3-.d.]pyrimidine-5-carboxylic acid: MS: [M+1]⁺=315.

e) 6-(4-methoxycarbonyl-phenyl)-4-oxo-3,4-dihydro-furo[2,3-.d.]pyrimidine-5-carboxylic acid Catalytic hydrogenation of 6-(4-methoxycarbonyl-phenyl)-4-oxo-3,4-dihydro-furo[2,3-.d.]pyrimidine-5-carboxylic acid benzylester gives the title compound.

Example 38

Dry-filled capsules: 5000 capsules, each comprising as active ingredient 0.25 g of one of the compounds of formula I mentioned in the preceding Examples, are prepared as follows:

| Composition | |
|---|---|
| active ingredient | 1250 g |
| talc | 180 g |
| wheat starch | 120 g |
| magnesium stearate | 80 g |
| lactose | 20 g |

Preparation process: The said substances are pulverised and forced through a sieve with a mesh width of 0.6 mm. 0.33 g portions of the mixture are filled into gelatin capsules using a capsule-filling machine.

Example 39

Soft capsules: 5000 soft gelatin capsules, each comprising as active ingredient 0.05 g of one of the compounds of formula I mentioned in the preceding Examples, are prepared as follows:

| Composition | |
|---|---|
| active ingredient | 250 g |
| PEG 400 | 1 liter |
| Tween 80 | 1 liter |

Preparation process: The pulverised active ingredient is suspended in PEG 400 (polyethylene glycol with Mr between about 380 and about 420, Fluka, Switzerland) and Tween® 80 (polyoxyethylene sorbitan monolaurate, Atlas Chem. Ind., Inc., USA, supplied by Fluka, Switzerland) and ground in a wet pulverizer to produce a particle size of about 1 to 3 μm. 0.43 g portions of the mixture are then introduced into soft gelatin capsules using a capsule-filling machine.

What is claimed is:

1. A compound of formula I

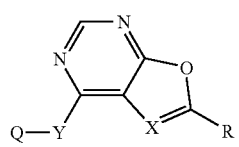

(I)

wherein X either signifies nitrogen or a carbon atom bearing a radical A;

A signifies hydrogen or —COOW, wherein W is hydrogen or alkyl, aryl, heterocyclyl or cycloalkyl, whereby each of these radicals is unsubstituted or substituted;

Y is NR', or O, whereby R' signifies hydrogen or alkyl;

R signifies phenyl which is substituted by nitro, amino, lower alkylpiperazinylcarbonyl, morpholinylcarbonyl, N,N-di-lower alkylcarbamoyl, N,N-di-lower alkylamino lower alkyl, lower alkylpiperazinyl lower alkvl or morpholinyl lower alkyl; and Q is aryl, aryl-alkyl, heterocyclyl, heterocyclyl-alkyl, cycloalkyl or cycloalkyl-alkyl, which are unsubstituted or substituted;

or a salt thereof.

2. A compound of formula I according to claim 1, wherein X either signifies nitrogen or signifies a carbon atom bearing a radical A;

A signifies hydrogen or —COOW, wherein W signifies alkyl or hydrogen;

Y is NP', or O, whereby R' signifies hydrogen or alkyl; and

Q is aryl, aryl lower alkyl or heterocyclyl, which are respectively unsubstituted or substituted;

or a salt thereof.

3. A compound of formula I according to claim 1, wherein X either signifies nitrogen or signifies a carbon atom bearing a radical A; A signifies hydrogen or —COOW, wherein W signifies alkyl or hydrogen;

and

Q signifies aryl or aryl lower alkyl;

or a salt thereof.

4. A compound of formula I according to claim 1, wherein X either signifies nitrogen, or a carbon atom bearing a radical A; wherein A signifies hydrogen;

and

Q is benzyl, phenylethyl or phenyl which is unsubstituted or substituted by one or more radicals, which, independently of one another, are selected from hydroxy, lower alkyl, lower alkoxy and halogen; pyridyl which is substituted by hydroxy or lower alkoxy; or indolyl which is substituted by halogen and lower alkyl;

or a salt thereof.

5. A compound of formula I according to claim 1, wherein X either signifies nitrogen or signifies a carbon atom bearing a radical A; A signifies hydrogen;

R is phenyl which is substituted by nitro or amino; and Q is benzyl, phenylethyl or phenyl, which is unsubstituted or is substituted by one or more radicals, which, independently of one another, are selected from hydroxy, lower alkoxy, and halogen or a salt thereof.

6. A compound of formula I according to claim 1, wherein X either signifies nitrogen or signifies a carbon atom bearing a radical A; A signifies hydrogen; R is phenyl which is substituted by amino; and Q is benzyl, phenylethyl or phenyl, which is substituted by one or more radicals, which, independently of one another, are selected from hydroxy, lower alkoxy, and halogen, or a salt thereof.

7. A compound according to claim 1, wherein X signifies nitrogen.

8. A compound according to claim 1, wherein X signifies a group CH.

9. A compound according to claim 1, wherein Y is NH or O.

10. A compound of formula I according to claim 1, selected from the group comprising 3-{2'-(4'-aminophenyl)oxazolo[5,4-d]pyrimidin-7'-ylamino}phenol;

3-{2'-(4"-nitrophenyl)oxazolo[5,4-d]pyrimidin-7'-ylamino}phenol;
7-(3"-chloroanilino)₂-(4'-aminophenyl)oxazolo[5,4-d]pyrimidine dihydrochloride;
7-(3"-chloroanilino)-2-(4'-nitrophenyl)oxazolo[5,4-d]pyrimidine;
4-{2'-(4"-aminophenyl)oxazolo[5,4-d]pyrimidin7'-ylamino}phenol;
4-{2'-(4"-nitrophenyl)oxazolo[5,4-d]pyrimidin-7'-ylamino}phenol;
7-(4"-chloroanilino)-2-(4'-aminophenyl)oxazolo[5,4-d]pyrimidine;
7-(4"-chloroanilino)-2-(4'-nitrophenyl)oxazolo[5,4-d]pyrimidine;
3-{2'-(3"-aminophenyl)oxazolo[5,4-d]pyrimidin-7'-ylamino}phenol;
3-{2'-(3"-nitrophenyl)oxazolo[5,4-d]pyrimidin-7'-ylamino}phenol;
7-(3"-chloroanilino)-2-(3'-aminophenyl)oxazolo[5,4-d]pyrimidine;
7-(3"-chloroanilino)-2-(3'-nitrophenyl)oxazolo[5,4-d]pyrimidine;
2-methoxy-5-{2'-(3"-aminophenyl)oxazolo[5,4-d]pyrimidin-7'-ylamino}phenol;
2-methoxy-5-{2'-(3"-nitrophenyl)oxazolo[5,4-d]pyrimidin-7'-ylamino}phenol;
4-(4-chloro-2-fluoranilino)-6-(4-aminophenyl)furo[2,3-d]pyrimidine;
4-(4-chloro-2-fluoranilino)-6-(4-nitrophenyl)furo[2,3-d]pyrimidine;
4-(3-chloroanilino)-6-(4-aminophenyl)furo[2,3-d]pyrimidine;
4-(3-chloroanilino)-6-(4-nitrophenyl)furo[2,3-d]pyrimidine;
4-(3-hydroxy-4-methoxyanilino)-6-(4-aminophenyl)furo[2,3-d]pyrimidine;
4-(3-hydroxy-4-methoxyanilino)-6-(4-nitrophenyl)furo[2,3-d]pyrimidine;
4-(3-hydroxy-4-methylanilino)-6-(4-aminophenyl)furo[2,3-d]pyrimidine;
4-(3-hydroxy-4-methylanilino)-6-(4-nitrophenyl)furo[2,3-d]pyrimidine;
4-(3-aminoanilino)-6-(4-aminophenyl)furo[2,3-d]pyrimidine;
4-(3-aminoanilino)-6-(4-nitrophenyl)furo[2,3-d]pyrimidine;
4-(1R-phenylethylamino)-6-(3-aminophenyl)furo[2,3-d]pyrimidine; and
4-(1R-phenylethylamino)-6-(3-nitrophenyl)furo[2,3-d]pyrimidine;
or a salt thereof.

11. A pharmaceutical preparation, comprising a compound of formula I, or a pharmaceutically acceptable salt thereof, according to claim 1, and at least one pharmaceutically acceptable carrier.

12. Process for the preparation of a compound of formula I illustrated in claim 1, comprising
(a) a compound of formula II

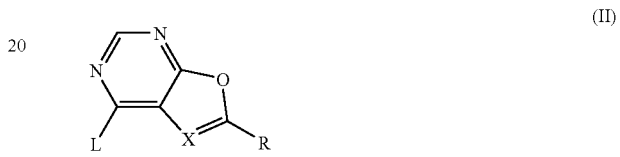

wherein X and R have the significances given for a compound of formula I in claim 1 and L is halogen with an amine, or phenol of formula III,

Q-YH            (III)

wherein Q has the significances given for compounds of formula I and Y is NR', or O, whereby R' signifies hydrogen or alkyl; wherein, if necessary, functional groups present in a compound of formula II and/or III, which are not to take part in the reaction, are present in protected form, and protecting groups that are present are cleaved;
and, if desired, converting a free compound of formula I into a salt; or converting a salt of a compound of formula I into another salt or the free compound of formula I.

* * * * *